(12) United States Patent
Watschke et al.

(10) Patent No.: US 7,993,261 B2
(45) Date of Patent: *Aug. 9, 2011

(54) METHOD AND APPARATUS FOR CYSTOCELE REPAIR

(75) Inventors: Brian P. Watschke, Eden Prairie, MN (US); Karen Pilney Montpetit, Mendota Heights, MN (US); Kimberly A. Anderson, Eagan, MN (US)

(73) Assignee: AMS Research Corporation, Minnetonka, MN (US)

( * ) Notice: Subject to any disclaimer, the term of this patent is extended or adjusted under 35 U.S.C. 154(b) by 480 days.

This patent is subject to a terminal disclaimer.

(21) Appl. No.: 12/059,117

(22) Filed: Mar. 31, 2008

(65) Prior Publication Data

US 2008/0183031 A1 Jul. 31, 2008

Related U.S. Application Data

(63) Continuation of application No. 10/840,646, filed on May 7, 2004, now Pat. No. 7,351,197.

(51) Int. Cl.
*A61F 2/00* (2006.01)

(52) U.S. Cl. ......................................... 600/30

(58) Field of Classification Search .............. 600/29–32, 600/37; 128/897–899, DIG. 25; 606/119, 606/148, 151–156, 222–225; 623/23.72
See application file for complete search history.

(56) References Cited

U.S. PATENT DOCUMENTS

| | | |
|---|---|---|
| 2,738,790 A | 3/1956 | Todt et al. |
| 3,124,136 A | 3/1964 | Usher |
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |

(Continued)

FOREIGN PATENT DOCUMENTS

DE 23 05 815 A1 8/1974

(Continued)

OTHER PUBLICATIONS

"Urinary Incontinence: Easier Operation" Article from La Libre Belgique, Wednesday, Oct. 15, 2003 (English translation provided).

(Continued)

*Primary Examiner* — John P Lacyk
(74) *Attorney, Agent, or Firm* — Kimberly K. Baxter; Gregory L. Koeller

(57) ABSTRACT

A method for cystocele repair comprising the steps of: establishing four pathways in tissue around a bladder of a patient, introducing a strap into each of said pathways, and positioning beneath said bladder of said patient a support member having each said strap connected thereto such that said bladder of said patient is supported by said support member and a bulge of said bladder into a vagina of said patient is reduced.

26 Claims, 28 Drawing Sheets

U.S. PATENT DOCUMENTS

| | | | |
|---|---|---|---|
| 4,128,100 A | 12/1978 | Wendorff | |
| 4,172,458 A | 10/1979 | Pereyra | |
| 4,204,541 A | 5/1980 | Kapitanov | |
| 4,235,238 A | 11/1980 | Ogiu et al. | |
| 4,246,660 A | 1/1981 | Wevers | |
| 4,265,231 A | 5/1981 | Scheller, Jr. et al. | |
| 4,441,497 A | 4/1984 | Paudler | |
| 4,509,516 A | 4/1985 | Richmond | |
| 4,632,100 A | 12/1986 | Somers et al. | |
| 4,775,380 A | 10/1988 | Seedhom et al. | |
| 4,857,041 A | 8/1989 | Annis et al. | |
| 4,865,031 A | 9/1989 | O'Keeffe | |
| 4,920,986 A | 5/1990 | Biswas | |
| 5,053,043 A | 10/1991 | Gottesman et al. | |
| 5,085,661 A | 2/1992 | Moss | |
| 5,112,344 A | 5/1992 | Petros | |
| 5,123,428 A | 6/1992 | Schwarz | |
| 5,188,636 A | 2/1993 | Fedotov | |
| 5,207,694 A | 5/1993 | Broome | |
| 5,209,756 A | 5/1993 | Seedhom et al. | |
| 5,250,033 A | 10/1993 | Evans et al. | |
| 5,256,133 A | 10/1993 | Spitz | |
| 5,281,237 A | 1/1994 | Gimpelson | |
| 5,328,077 A | 7/1994 | Lou | |
| 5,336,239 A | 8/1994 | Gimpelson | |
| 5,337,736 A | 8/1994 | Reddy | |
| 5,362,294 A | 11/1994 | Seitzinger | |
| 5,368,595 A | 11/1994 | Lewis | |
| 5,383,904 A | 1/1995 | Totakura et al. | |
| 5,386,836 A | 2/1995 | Biswas | |
| 5,403,328 A | 4/1995 | Shallman | |
| 5,413,598 A | 5/1995 | Moreland | |
| 5,439,467 A | 8/1995 | Benderev et al. | |
| 5,520,700 A | 5/1996 | Beyar et al. | |
| 5,520,703 A | 5/1996 | Essig et al. | |
| 5,544,664 A | 8/1996 | Benderev et al. | |
| 5,562,685 A | 10/1996 | Mollenauer et al. | |
| 5,562,689 A | 10/1996 | Green et al. | |
| 5,571,139 A | 11/1996 | Jenkins, Jr. | |
| 5,591,163 A | 1/1997 | Thompson | |
| 5,611,515 A | 3/1997 | Benderev et al. | |
| 5,628,756 A | 5/1997 | Barker, Jr. et al. | |
| 5,633,286 A | 5/1997 | Chen | |
| 5,662,683 A | 9/1997 | Kay | |
| 5,669,935 A | 9/1997 | Rosenman et al. | |
| 5,683,349 A | 11/1997 | Makower et al. | |
| 5,807,403 A | 9/1998 | Beyar et al. | |
| 5,810,882 A | 9/1998 | Bolduc et al. | |
| 5,836,314 A | 11/1998 | Benderev et al. | |
| 5,836,315 A | 11/1998 | Benderev et al. | |
| 5,840,011 A | 11/1998 | Landgrebe et al. | |
| 5,842,478 A | 12/1998 | Benderev et al. | |
| 5,860,425 A | 1/1999 | Benderev et al. | |
| 5,899,909 A | 5/1999 | Claren et al. | |
| 5,904,696 A | 5/1999 | Rosenman | |
| 5,919,232 A | 7/1999 | Chaffringeon et al. | |
| 5,934,283 A | 8/1999 | Willem et al. | |
| 5,935,122 A | 8/1999 | Fourkas et al. | |
| 5,935,138 A | 8/1999 | McJames, II et al. | |
| 5,944,732 A | 8/1999 | Raulerson et al. | |
| 5,972,000 A | 10/1999 | Beyar et al. | |
| 5,988,171 A | 11/1999 | Sohn et al. | |
| 5,992,269 A | 11/1999 | Puig et al. | |
| 5,997,554 A | 12/1999 | Thompson | |
| 6,010,447 A | 1/2000 | Kardjian | |
| 6,030,393 A | 2/2000 | Corlew | |
| 6,031,148 A | 2/2000 | Hayes et al. | |
| 6,042,534 A | 3/2000 | Gellman et al. | |
| 6,042,536 A | 3/2000 | Tihon et al. | |
| 6,048,351 A | 4/2000 | Gordon et al. | |
| 6,050,937 A | 4/2000 | Benderev | |
| 6,053,935 A | 4/2000 | Brenneman et al. | |
| 6,068,591 A | 5/2000 | Bruckner et al. | |
| 6,071,290 A | 6/2000 | Compton | |
| 6,099,538 A | 8/2000 | Moses et al. | |
| 6,106,545 A | 8/2000 | Egan | |
| 6,110,101 A | 8/2000 | Tihon et al. | |
| 6,117,067 A | 9/2000 | Gil-Vernet | |
| 6,168,611 B1 | 1/2001 | Risvi | |
| 6,221,005 B1 | 4/2001 | Bruckner et al. | |
| 6,273,852 B1 | 8/2001 | Lehe et al. | |
| 6,302,840 B1 | 10/2001 | Benderev | |
| 6,306,079 B1 | 10/2001 | Trabucco | |
| 6,328,744 B1 | 12/2001 | Harari et al. | |
| 6,334,446 B1 | 1/2002 | Beyar | |
| 6,352,553 B1 | 3/2002 | van de Burg et al. | |
| 6,367,353 B2 | 4/2002 | Brucart Puig et al. | |
| 6,382,214 B1 | 5/2002 | Raz et al. | |
| 6,406,423 B1 | 6/2002 | Scetbon | |
| 6,406,480 B1 | 6/2002 | Beyar et al. | |
| 6,475,139 B1 | 11/2002 | Miller | |
| 6,478,727 B2 | 11/2002 | Scetbon | |
| 6,482,214 B1 | 11/2002 | Sidor, Jr. et al. | |
| 6,494,906 B1 | 12/2002 | Owens | |
| 6,502,578 B2 | 1/2003 | Raz et al. | |
| 6,530,943 B1 | 3/2003 | Hoepffner et al. | |
| 6,582,443 B2 | 6/2003 | Cabak et al. | |
| 6,626,917 B1 | 9/2003 | Craig | |
| 6,663,633 B1 | 12/2003 | Pierson, II | |
| 6,911,003 B2 * | 6/2005 | Anderson et al. | 600/30 |
| 7,351,197 B2 * | 4/2008 | Montpetit et al. | 600/30 |
| 2001/0000533 A1 | 4/2001 | Kovac | |
| 2001/0049467 A1 | 12/2001 | Lehe et al. | |
| 2002/0022841 A1 | 2/2002 | Kovac | |
| 2002/0028980 A1 | 3/2002 | Thierfelder et al. | |
| 2002/0055748 A1 | 5/2002 | Gellman et al. | |
| 2002/0058959 A1 | 5/2002 | Gellman | |
| 2002/0068948 A1 | 6/2002 | Stormby et al. | |
| 2002/0072694 A1 | 6/2002 | Snitkin et al. | |
| 2002/0077526 A1 | 6/2002 | Kammerer et al. | |
| 2002/0078964 A1 | 6/2002 | Kovac et al. | |
| 2002/0091373 A1 | 7/2002 | Berger | |
| 2002/0099258 A1 | 7/2002 | Staskin et al. | |
| 2002/0099259 A1 | 7/2002 | Anderson et al. | |
| 2002/0099260 A1 | 7/2002 | Suslaine et al. | |
| 2002/0107430 A1 | 8/2002 | Neisz et al. | |
| 2002/0107525 A1 | 8/2002 | Harari et al. | |
| 2002/0115906 A1 | 8/2002 | Miller | |
| 2002/0128670 A1 | 9/2002 | Ulmsten et al. | |
| 2002/0138025 A1 | 9/2002 | Gellman et al. | |
| 2002/0147382 A1 | 10/2002 | Neisz et al. | |
| 2002/0151762 A1 | 10/2002 | Rocheleau et al. | |
| 2002/0151909 A1 | 10/2002 | Gellman et al. | |
| 2002/0151910 A1 | 10/2002 | Gellman et al. | |
| 2002/0156487 A1 | 10/2002 | Gellman et al. | |
| 2002/0156488 A1 | 10/2002 | Gellman et al. | |
| 2002/0165566 A1 | 11/2002 | Ulmsten | |
| 2002/0188169 A1 | 12/2002 | Kammerer et al. | |
| 2003/0004395 A1 | 1/2003 | Therin | |
| 2003/0009181 A1 | 1/2003 | Gellman et al. | |
| 2003/0023136 A1 | 1/2003 | Raz | |
| 2003/0023137 A1 | 1/2003 | Gellman | |
| 2003/0023138 A1 | 1/2003 | Luscombe | |
| 2003/0036676 A1 | 2/2003 | Scetbon | |
| 2003/0045774 A1 | 3/2003 | Staskin et al. | |
| 2003/0045892 A1 | 3/2003 | Kaladelfos | |
| 2003/0050530 A1 | 3/2003 | Neisz et al. | |
| 2003/0065246 A1 | 4/2003 | Inman et al. | |
| 2003/0065402 A1 | 4/2003 | Anderson et al. | |
| 2003/0100954 A1 | 5/2003 | Schuldt-Hempe et al. | |
| 2003/0114866 A1 | 6/2003 | Ulmsten et al. | |
| 2003/0130670 A1 | 7/2003 | Anderson et al. | |
| 2003/0149440 A1 | 8/2003 | Kammerer et al. | |
| 2003/0171644 A1 | 9/2003 | Anderson et al. | |
| 2003/0176762 A1 | 9/2003 | Kammerer | |
| 2003/0199732 A1 | 10/2003 | Suslian et al. | |
| 2003/0220538 A1 | 11/2003 | Jacquetin | |
| 2004/0039453 A1 | 2/2004 | Anderson et al. | |

FOREIGN PATENT DOCUMENTS

| | | |
|---|---|---|
| DE | 42 20 283 C2 | 12/1993 |
| DE | 43 04 353 A1 | 4/1994 |
| DE | 101 38 950 A1 | 2/2003 |
| DE | 102 11 360 A1 | 10/2003 |
| EP | 0 470 308 A1 | 2/1992 |
| EP | 0 643 945 A2 | 3/1995 |
| EP | 0 650 703 A1 | 5/1995 |

| | | | |
|---|---|---|---|
| EP | 1 093 758 A1 | 4/2001 | |
| SU | 1225547 A | 4/1986 | |
| SU | 1342486 A1 | 10/1987 | |
| WO | WO 93/17635 A1 | 9/1993 | |
| WO | WO 93/19678 A2 | 10/1993 | |
| WO | WO 97/16121 A1 | 5/1997 | |
| WO | WO 98/19606 A1 | 5/1998 | |
| WO | WO 98/35606 A2 | 8/1998 | |
| WO | WO 98/35616 A1 | 8/1998 | |
| WO | WO 98/35632 A | 8/1998 | |
| WO | WO 98/35632 A1 | 8/1998 | |
| WO | WO 99/52450 A1 | 10/1999 | |
| WO | WO 00/13601 A1 | 3/2000 | |
| WO | WO 00/18319 A1 | 4/2000 | |
| WO | WO 00/57812 A1 | 10/2000 | |
| WO | WO 00/64370 A1 | 11/2000 | |
| WO | WO 00/74594 A1 | 12/2000 | |
| WO | WO 00/74613 A1 | 12/2000 | |
| WO | WO 00/74633 A2 | 12/2000 | |
| WO | WO 01/26581 A1 | 4/2001 | |
| WO | WO 01/39670 A1 | 6/2001 | |
| WO | WO 01/45589 A1 | 6/2001 | |
| WO | WO 01/56499 A1 | 8/2001 | |
| WO | WO 01/78609 A2 | 10/2001 | |
| WO | WO 02/02031 A1 | 1/2002 | |
| WO | WO02/19944 A2 | 3/2002 | |
| WO | WO 02/26108 A2 | 4/2002 | |
| WO | WO 02/28312 A1 | 4/2002 | |
| WO | WO 02/32284 A2 | 4/2002 | |
| WO | WO 02/34124 A2 | 5/2002 | |
| WO | WO 02/38079 A2 | 5/2002 | |
| WO | WO 02/39890 A2 | 5/2002 | |
| WO | WO 02/069781 A2 | 9/2002 | |
| WO | WO 02/071953 A2 | 9/2002 | |
| WO | WO 02/078552 A1 | 10/2002 | |
| WO | WO 03073960 | 9/2003 | |
| WO | WO 2004/016196 A2 | 2/2004 | |
| WO | WO 2004/019786 A1 | 3/2004 | |
| WO | WO 2004091443 | 10/2004 | |

OTHER PUBLICATIONS

Aldridge, Albert H., B.S., M.D., F.A.C.S., "Transplantation of Fascia for Relief of Urinary Stress Incontinence" Am. J. of Obstet. and Gynec., vol. 44, pp. 398-411 (1948).

Araki, Tohru, et al, "The Loop-Loosening Procedure for Urination Difficulties After Stamey Suspension of the Vesical Neck" The Journal of Urology, vol. 144, pp. 319-323, (Aug. 1990) American Urological Association, Inc.

Asmussen, M., et al., "Simultaneous Urethro-Cystometry With a New Technique" Scand J Urol Nephrol 10, pp. 7 11 (1976).

Beck, Peter R. et al., "Treatment of Urinary Stress Incontinence With Anterior Colporrhaphy" Obstetrics and Gynecology, vol. 59 (No. 3), pp. 269-274 (Mar. 1982).

Benderev, Theodore V., M.D., "Anchor Fixation and Other Modifications of Endoscopic Bladder Neck Suspension" Urology, vol. 40, No. 5, pp. 409-418 (Nov. 1992).

Benderev, Theodore V., MD, "A Modified Percutaneous Outpatient Bladder Neck Suspension System" Journal of Urology, vol. 152, pp. 2319-2320 (Dec. 1994).

Bergman, Arieh, M.D. et al., "Three surgical procedures for genuine stress incontinence: Five-year follow-up of a prospective randomized study" Am. J. Obstet Gynecol, vol. 173 No. 1, pp. 66-71 (Jul. 1995).

Blaivas, Jerry G., "Commentary: Pubovaginal Sling Procedure" Surgery for Female Urinary Incontinence, pp. 93-101 (1990).

Blaivas, Jerry G., et al., "Pubovaginal Fascial Sling for the Treatment of Complicated Stress Urinary Incontinence" The Journal of Urology, vol. 145, pp. 1214-1218 (Jun. 1991) American Urological Association, Inc.

Blaivas, Jerry G., M.D., et al., "Type III Stress Urinary Incontinence: Importance of Proper Diagnosis and Treatment" Gynecology and Obstetrics Surgical Forum, 35, pp. 473-475 (1984).

Bryans, Fred E., M.D., F.R.C.S.(C.), "Marlex gauze hammock sling operation with Cooper's ligament attachment in the management of recurrent urinary stress incontinence" Am. J. Obstet. Gynecol., vol. 133, No. 3, pp. 292-294 (Feb. 1, 1979).

Burch, John C., M.D., "Urethrovaginal fixation to Cooper's ligament for correction of stress incontinence, cystocele, and prolapse" Am. J. Obstet. & Gynecol., vol. 81 No. 2, pp. 281-290 (Feb. 1961).

Choe, Jong M., et al., "Gore-Tex Patch Sling: 7 Years Later" Urology, 54 (4) pp. 641-646 (1999) Elsevier Science Inc.

Chu, C.C., and Welch, L., "Characterization of Morphologic and Mechanical Properties of Surgical Mesh Fabrics" Journal of Biomedical Materials Research, vol. 19, pp. 903-916 (1985) © 1985 John Wiley & Sons, Inc.

Dargent, D., et al. Pose d'un ruban sous uretral oblique par voie obturatrice dans le traitement de l'incontinence urinaire feminine, Gynecol Obstel Fertil 2002; 30: pp. 576-582 (2002) (English translation provided).

Das, Sakti et al., "Laparoscopic Colpo-Suspension" The Journal of Urology, vol. 154, pp. 1119-1121 (Sep. 1995).

de Leval, Jean "Novel Surgical Technique for the Treatment of Female Stress Urinary Incontinence: Transobturator Vaginal Tape Inside-Out" European Urology 44 pp. 724-730 (2003).

Decter, Ross M., "Use of the Fascial Sling for Neurogenic Incontinence: Lessons Learned" The Journal of Urology, vol. 150, pp. 683-686, (Aug. 1993) American Urological Association, Inc.

DeLancey, John O. L., M.D., "Structural support of the urethra as it relates to stress urinary incontinence: The hammock hypothesis" Am. J Obstet Gynecol, pp. 1713-1723 (Jun. 1994).

Delorme, "La bandelette trans-obturatrice: un procede mini-invasif pour traiter l'incontinence urinaire d'effort de la femme", Urologie de la Femme, Progres en Urologie (2001), 11, 1306-1313 (Sep. 2001) (English translation provided).

Delorme, Emmanuel et al., "Transobturator Tape (Uratape®): A New Minimally-Invasive Procedure to Treat Female Urinary Incontinence" European Urology 45 (2004) 203-207 (Dec. 2003).

Dietz, H.P., et al., "Mechanical Properties of urogynecologic Implant Materials" International Urogynecology Journal (2003) 14:239-243 (Aug. 5, 2003).

Enzelsberger, H., et al., "Urodynamic and Radiologic Parameters Before and After Loop Surgery for Recurrent Urinary Stress Incontinence" Acta Obstet Gynecol Scand 1990; 69 pp. 51-54 (1990).

Eriksen, Bjarne C., et al., "Long-Term Effectiveness of the Burch Colposuspension in Female Urinary Stress Incontinence" Acta Obstet Gynecol Scand 1990; 69 pp. 45-50 (1990).

Falconer, C. et al., "Clinical Outcome and Changes in Connective Tissue Metabolism After Intravaginal Slingplasty in Stress Incontinent Women" International Urogynecol J. vol. 7, pp. 133-137, (1996).

Falconer, C., et al., "Influence of Different Sling Materials on Connective Tissue Metabolism in Stress Urinary Incontinent Women" International Urogynecology Journal, (2001) (Supp. 2) pp. S19-S23 (2001).

Gilja, Ivan et all, "A Modified Raz Bladder Neck Suspension Operation (Transvaginal Burch)" The Journal of Urology, vol. 153, pp. 1455-1457 (May 1995).

Gittes, Ruben F., et al, "No-Incision Pubovaginal Suspension for Stress Incontinence" The Journal of Urology, vol. 138, pp. 568-570 (Sep. 1987).

Handa, Victoria L., M.D. et al., "Banked Human Fascia Lata for the Suburethral Sling Procedure: A Preliminary Report" Obstetrics and Gynecology, vol. 88, No. 6, pp. 1045-1049 (Dec. 1996).

Henriksson, L., M.D. et al., "A urodynamic evaluation of the effects of abdominal urethrocystopexy and vaginal sling urethroplasty in women with stress incontinence" Am. J. Gynecol, pp. 77-82 (May 1, 1978).

Hershorn, Sender, M.D. et al., "Gynecare TVT With Abdominal Guides Early Clinical Experience" Gynecare TVT, Marketing Material, Gynecare Worldwide (May 2002), 12 pages (May 2002).

Hodgkinson, C. Paul, M.D., et al., "Urinary Stress Incontinence in the Female—III. Round-ligament technic for retropubic suspension of the urethra" Obstetrics and Gynecology, vol. 10, No. 5, pp. 493-499 (Nov. 1957).

Hohenfellner, Rudolf, et al., "Sling Procedures" Surgery of Female Incontinence—Second Edition, Chapter 7, pp. 105-113, Springer-Verlag (May 1, 1986).

Holschneider, C.H., et al., "The Modified Pereyra Procedure in Recurrent Stress Urinary Incontinence: A 15-year Review" Obstetrics & Gynecology, vol. 83, No. 4, pp. 573-578 (Apr. 1994).
Horbach, Nicollette S., "Suburethral Sling Procedures" Urolgynecology and Urodynamics Theory and Practice, Fourth Edition, Chapter 42, pp. 569-579, Williams & Wilkins (1996).
Horbach, Nicollette S., et al., "A Suburethral Sling Procedure with Polytetrafluoroethylene for the Treatment of Genuine Stress Incontinence in Patients with Low Urethral Closure Pressure" Obstetrics & Gynecology, vol. 71, No. 4, pp. 648-652 (Apr. 1988).
Iglesia, C.B., et al., "The Use of Mesh in Gynecologic Surgery" International Urogynecology Journal (1997) 8:105-115, Springer-Verlag London Ltd. (1997).
Ingelman-Sundberg, A., et al., "Surgical Treatment of Female Urinary Stress Incontinence" Contr. Gynec. Obstet. vol. 10, pp. 51-69 (Karger. Basel 1983).
Jeffcoate, T.N.A., M.D., F.R.C.S.E., F.R.C.O.G., "The Results of the Aldridge Sling Operation for Stress Incontinence" J Obstet Gynaecol Br Emp., 63(1) pp. 36-39 (Feb. 1956).
Karram, Mickey M., M.D. et al., "Patch Procedure: Modified Transvaginal Fascia Late Sling for Recurrent or Severe Stress Urinary Incontinence" Obstetrics & Gynecology, vol. 75, No. 3, Part 1, pp. 461-463 (Mar. 1990).
Kersey, J., "The gauze hammock sling operation in the treatment of stress incontinence" British Journal of Obstetrics and Gynaecology, vol. 90 pp. 945-949, (Oct. 1983).
Klutke, Carl et al., "The Anatomy of Stress Incontinence: Magentic Resonance Imaging of the Female Bladder Neck and Urethra" The Journal Urology, vol. 143, pp. 563-566 (Mar. 1990).
Klutke, John James et al., "Transvaginal Bladder Neck Suspension to Cooper's Ligament: A Modified Pereyra Procedure" Obstetrics & Gynecology, vol. 88, No. 2, pp. 294-296 (Aug. 1996).
Klutke, John, M.D. et al., "The promise of tension-free vaginal tape for female SUI" Contemporary Urology, pp. 59-60, 65-66, 69-70, 73 (Oct. 2000).
Korda, Andrew, et al., "Experience with Silastic Slings for Female Urinary Incontinence" Aust NZ J Obstet Gynaecol, vol. 29, pp. 150-154 (1989).
Kovac, S. Robert, et al, "Pubic Bone Suburethral Stabilization Sling for Recurrent Urinary Incontinence" Obstetrics & Gynecology, vol. 89, No. 4, pp. 624-627 (Apr. 1997).
Kovac, S. Robert, et al, "Pubic Bone Suburethral Stabilization Sling: A Long Term Cure for SUI?" Contemporary OB/GYN, 8 pages (Feb. 1998).
Kovac, S. Robert, "Follow-up of the Pubic Bone Suburethral Stabilization Sling Operation for Recurrent Urinary Incontinence (Kovac Procedure)" Journal of Pelvic Surgery, pp. 156-160 (May 1999).
Leach, Gary E., et al, "Female Stress Urinary Incontinence Clinical Guidelines Panel Report on Surgical Management of Female Stress Urinary Incontinence" American Urological Association, vol. 158, pp. 875-880 (Sep. 1997).
Leach, Gary E., MD, "Bone Fixation Technique for Transvaginal Needle Suspension" Urology vol. XXXI, No. 5, pp. 388-390 (May 1988).
Letters to the Editor, R. Villet's response to the article by D. Dargent et al., "Placement of an oblique transobturator suburethral tape in the treatment of female urinary incontinence", Gynecology Obstetrics & Fertility 31, pp. 96-101 (2003) (English translation provided).
Lichtenstein, Irving L., M.D., et al., "The Tension-Free Hernioplasty" The American Journal of Surgery, vol. 157, pp. 188-193 (Feb. 1989).
Loughlin, Kevin R., et al., "Review of an 8-Year Experience With Modifications of Endoscopic Suspension of the Bladder Neck for Female Stress Urinary Incontinence" The Journal of Urology, vol. 143, pp. 44-45 (Jan. 1990).
Marshall, Victor Fray, M.D., F.A.C.S. et al., "The Correction of Stress Incontinence by Simple Vesicourethral Suspension" Surgery, Gynecology and Obstetrics, vol. 88, pp. 509-518 (1949).
Mascio, Valenzio C., M.D., "Therapy of Urinary Stress Incontinence in Women Using Mitek GII Anchors" Mitek Surgical Products, Inc., 5 pages (1993).
McGuire, Edward J. et al., "Abdominal Fascial Slings" Female Urology 2nd ed. (Raz. S. ed.). W.B. Saunders Company, Chapter 31, pp. 369-375 (1996).
McGuire, Edward J. et al., "Experience With Pubovaginal Slings for Urinary Incontinence at the University of Michigan" The Journal of Urology, vol. 138, pp. 525-526 (Sep. 1987).
McGuire, Edward J., et al., "Pubovaginal Sling Procedure for Stress Incontinence" The Journal of Urology, vol. 119, pp. 82-84 (Jan. 1978) The Williams & Wilkins Co.
McGuire, Edward J., M.D., "Abdominal Procedures for Stress Incontinence" Symposium on Female Urology, Urologic Clinics of North America—vol. 12, No. 2, pp. 285-290 (May 1985).
McIndoe, G. A. J., et al., "The Aldridge Sling Procedure in the Treatment of Urinary Stress Incontinence" Aust NZ J Obstet Gynaecol, vol. 27, pp. 238-239 (1987).
McKiel, Charles F., Jr. et al., "Marshall-Marchetti Procedure: Modification" 1st Journal in Urology, vol. 96, pp. 737-739 (Nov. 1966) The Williams & Wilkins Co.
Moir, J. Chassar, "The Gauze-Hammock Operation (A Modified Aldridge Sling Prcedure)" The Journal of Obstetrics and Gynaecology of the British Commonwealth, vol. 75 No. 1, pp. 1-9 (Jan. 1968).
Morgan, J.E., M.D. et al., "The Marlex Sling Operation for the Treatment of Recurrent Stress Urinary Incontinence: A 16-Year Review", Am. J. Obstet. Gynecol., vol. 151, No. 2, pp. 224-226 (Jan. 15, 1985).
Morgan, J.E., M.D., "A sling operation, using Marlex Polypropylene mesh, for treatment of recurrent stress incontinence", Amer. J. Obstet. Gynecol., vol. 106, No. 3, pp. 369-377 (Feb. 15, 1970).
Narik, G., M.D., "A simplified sling operation suitable for routine use" Am. J. Obst. & Gynec., vol. 84, No. 3, pp. 400-405 (Aug. 1, 1962).
Nichols, David H., MD, Facog, "The Mersilene Mesh Gauze-Hammock for Severe Urinary Stress Incontinence" Obstetrics and Gynecology, vol. 41, No. 1, pp. 88-93 (Jan. 1973).
Nickel, Rafael F., et al., "Evaluation of a Transpelvic Sling Procedure With and Without Colposuspension for Treatment of Female Dogs With Refractory Urethral Sphincter Mechanism Incompetence" Veterinary Surgery, vol. 27, pp. 94-104, (1998), The American College of Veterinary Surgeons.
Norris, Jeffrey P., M.D., et al., "Use of Synthetic Material in Sling Surgery: A Minimally Invasive Approach" Journal of Endourology, vol. 10 No. 3, pp. 227-230 (Jun. 1996) Mary Ann Liebert, Inc.
O'Donnell, Pat D., M.D., "Combined Raz Urethral Suspension and McGuire Pubovaginal Sling for Treatment of Complicated Stress Urinary Incontinence" Journal of The Arkansas Medical Society, vol. 88, No. 8, pp. 389-392 (Jan. 1992).
Parra, R. 0., et al "Experience with a Simplified Technique for the Treatment of Female Stress Urinary Incontinence" British Journal of Urology, vol. 66, pp. 615-617 (1990).
Pelosi, Marco A., II, et al., "New Tranobturator Sling Reduces Risk of Injury" OBG Management, pp. 17-20, 30, 32, 35-38 (Jul. 2003).
Pelosi, Marco Antonio III et al., "Pubic Bone Suburethral Stabilization Sling: Laparoscopic Assessment of a Transvaginal Operation for the Treatment of Stress Urinary Incontinence" Journal of Laparoendoscopic & Advanced Surgical Techniques, vol. 9, No. 1 pp. 45-50 (1999).
Pereyra, Armand J. et al, "Pubourethral Supports in Perspective: Modified Pereyra Procedure for Urinary Incontinence" Obstetrics and Gynecology, vol. 59, No. 5, pp. 643-648 (May 1982).
Pereyra, Armand J., M.D., F.A.C.S., "A Simplified Surgical Procedure for the Correction of Stress Incontinence in Women" West J. Surg. Obst. & Gynec. pp. 223-226 (Jul.-Aug. 1959).
Petros, P. E. Papa, "Medium-term Follow-up of the Intravaginal Slingplasty Operation Indicates Minimal Deterioration of Urinary Continence With Time" Aust NZ J Obstet Gynaecol, vol. 39, No. 3, pp. 354-356 (1999) (International Urogynecology Journal and Pelvic Floor Dysfunction, Reprinted from vol. 7, No. 3, pp. 133-137 (1996)).
Petros, P. E. Papa, "New Ambulatory Surgical Methods Using an Anatomical Classification of Urinary Dysfunction Improve Stress, Urge and Abnormal Emptying" Int-Urogynecol-J-Pelvic-Floor-Dysfunct, Aug. 5, pp. 270-277 (1997).

Petros, P. E. Papa, et al., "An analysis of rapid pad testing and the history for the diagnosis of stress incontinence" Acta Obstet Gynecol Scand 71, pp. 529-536 (1992).

Petros, P. E. Papa, et al., "An Anatomical Basis for Success and Failure of Female Incontinence Surgery" Scand J Urol Nephrol, Suppl. No. 153, pp. 55-60 (1993).

Petros, P. E. Papa, et al., "An integral theory of female urinary incontinence—Experimental and clinical considerations" Acta Obstet Gynecol Scand, vol. 69, Suppl. 153, pp. 7-31 (1990), The Scandinavian Association of Obstetricians and Gynecologists.

Petros, P. E. Papa, et al., "Anchoring the midurethra restores bladder-neck anatomy and continence" The Lancet, vol. 354, pp. 997-998 (Sep. 18, 1999).

Petros, P. E. Papa, et al., "Bladder Instability in Women: A Premature Activation of the Micturition Reflex" Neurourology and Urodynamics, vol. 12, pp. 235-238 (1993).

Petros, P. E. Papa, et al., "Cough Transmission Ratio: An Indicator of Suburethral Vaginal Wall Tension Rather Than Urethral Closure?" Acta Obstet Gynecol Scand, vol. 69 Suppl. 153, pp. 37-39 (1990).

Petros, P. E. Papa, et al., "Cure of Stress Incontinence by Repair of External Anal Spincter: Two Case Reports" Acta Obstet Gynecol Scand, vol. 69 Suppl. 153, p. 75 (1990).

Petros, P. E. Papa, et al., "Cure of Urge Incontinence by the Combined Intravaginal Sling and Tuck Operation" Acta Obstet Gynecol Scand, vol. 69 Suppl. 153, pp. 61-62 (1990).

Petros, P. E. Papa, et al., "Further Development of the Intravaginal Slingplasty Procedure—IVS III—(with midline tuck)" Scand J Urol Nephrol, Suppl. 153, pp. 69-71 (1993).

Petros, P. E. Papa, et al., "Non Stress Non Urge Female Urinary Incontinence—Diagnosis and Cure: A Preliminary Report" Acta Obstet Gynecol Scand, vol. 69 Suppl. 153. pp. 69-70 (1990).

Petros, P. E. Papa, et al., "Part I: Theoretical, Morphological, Radiographical Correlations and Clinical Perspective" Scand J Urol Nephrol, Suppl. 153. pp. 5-28 (1993).

Petros, P. E. Papa, et al., "Part II: The Biomechanics of Vaginal Tissue and Supporting Ligaments With Special Relevance to the Pathogenesis of Female Urinary Incontinence" Scand J Urol Nephrol, Suppl. No. 153, pp. 29-40 (1993).

Petros, P. E. Papa, et al., "Part III: Surgical Principles Deriving From the Theory" Scand J Urol Nephrol, Suppl. No. 153, pp. 41-52 (1993).

Petros, P. E. Papa, et al., "Part IV: Surgical Applications of the Theory—Development of the Intravaginal Sling Plasty (IVS) Procedure" Scand J Urol Nephrol, Suppl. No. 153, pp. 53-54 (1993).

Petros, P. E. Papa, et al., "Pregnancy Effects on the Intravaginal Sling Operation" Acta Obstet Gynecol Scand, vol. 69 Suppl. 153, pp. 77-79 (1990).

Petros, P. E. Papa, et al., "The Autogenic Ligament Procedure: A Technique for Planned Formation of an Artificial Neo-Ligament" Acta Obstet Gynecol Scand, vol. 69 Suppl. 153, pp. 43-51 (1990).

Petros, P. E. Papa, et al., "The Combined Intravaginal Sling and Tuck Operation. An Ambulatory Procedure for Cure of Stress and Urge Incontinence" Acta Obstet Gynecol Scand, vol. 69 Suppl 153, pp. 53-59 (1990).

Petros, P. E. Papa, et al., "The Development of the Intravaginal Slingplasty Procedure: IVS II—with bilateral 'tucks')", Scand J Urol Nephrol, Suppl. 153. pp. 61-67 (1993).

Petros, P. E. Papa, et al., "The Free Graft Procedure for Cure of the Tethered Vagina Syndrome" Scand J Urol Nephrol, Suppl. No. 153, pp. 85-87 (1993).

Petros, P. E. Papa, et al., "The Further Development of the Intravaginal Slingplasty Procedure: IVS IV—(with "double-breasted" unattached vaginal flap repair and "free" vaginal tapes)" Scand J Urol Nephrol, Suppl. No. 153, pp. 73-79 (1993).

Petros, P. E. Papa, et al., "The Intravaginal Slingplasty Procedure: IVS VI—further development of the 'double-breasted' vaginal flap repair—attached flap" Scand J Urol Nephrol, Suppl. No. 153, pp. 81-84 (1993).

Petros, P. E. Papa, et al., "The Posterior Fornix Syndrome: A Multiple Symptom Complex of Pelvic Pain and Abnormal Urinary Symtoms Deriving From Laxity in the Posterior Fornix of Vagina" Scand J Urol Nephrol, Suppl. No. 153, pp. 89-93 (1993).

Petros, P. E. Papa, et al., "The Role of a Lax Posterior Vaginal Fornix in the Causation of Stress and Urgency Symptoms: A Preliminary Report" Acta Obstet Gynecol Scand, vol. 69 Suppl. 153, pp. 71-73 (1990).

Petros, P. E. Papa, et al., "The Tethered Vagina Syndrome, Post Surgical Incontinence and I-Plasty Operation for Cure" Acta Obstet Gynecol Scand, vol. 69 Suppl. 153, pp. 63-67 (1990).

Petros, P. E. Papa, at al., "The Tuck Procedure: A Simplified Vaginal Repair for Treatment of Female Urinary Incontinence" Acta Obstet Gynecol Scand, vol. 69 Suppl. 153, pp. 41-42 (1990).

Petros, P. E. Papa, et al., "Urethral Pressure Increase on Effort Originates From Within the Urethra, and Continence From Musculovaginal Closure" Neurourology and Urodynamics, vol. 14, pp. 337-350 (1995).

Petros, P. E. Pappa, "Development of Generic Models for Ambulatory Vaginal Surgery—Preliminary Report" International Urogynecology Journal, 9 pages (1998).

Pourdeyhimi, "Porosity of surgical mesh fabrics: New technology", J. Biomed. Mater. Res.: Applied Biomaterials, vol. 23, No. A1, pp. 145-152 (1989), © 1989 John Wiley & Sons, Inc.

Rackley, Raymond R., M.D., et al. "Tension-free Vaginal Tape and Percutaneous Vaginal Tape Sling Procedures" Techniques in Urology, vol. 7, No. 2, pp. 90-100 (2001).

Rackley, Raymond, M.D., "Synthetic slings: Five steps for successful placement" Urology Times, pp. 46, 48-49 (Jun. 2000).

Raz, Shlomo, et al., The Raz Bladder Neck Suspension Results in 206 Patients, The Journal of Urology, pp. 845-850 (Sep. 1992).

Raz, Shlomo, M.D. et al., "Female Urology—Second Edition" University of California at Los Angeles School of Medicine, articles pp. 80-86, 369-381, 392-394, 395-398, 435-442, (1996) W.B. Saunders Company.

Raz, Shlomo, M.D., "Modified Bladder Neck Suspension for Female Stress Incontinence" Urology, vol. XVII, No. 1, pp. 82-85 (Jan. 1981) University of California Health Sciences Center, Los Angeles, CA.

Richardson, David A., M.D., et al., "Delayed Reaction to the Dacron Buttress Used in Urethropexy" The Journal of Reproductive Medicine, vol. 29 No. 9, pp. 689-692 (Sep. 1984).

Ridley, John H., M.D., "Appraisal of the Goebell-Frangenheim-Stoeckel sling procedure" Am. J. Obst. & Gynec. vol. 95, No. 5, pp. 714-721 (Jul. 1966).

Roberts, Henry, M.D., M.R.C.O.G., "Cystourethrography in Women" Ethel Bovce University Fellowship vol. 25 No. 293, pp. 253-259 (May 1952) University of Liverpool.

Sloan, W. R., et al., "Stress Incontinence of Urine: A Retrospective Study of the Complications and Late Results of Simple Suprapubic Suburethral Fascial Slings" The Journal of Urology, vol. 110, pp. 533-536 (Nov. 1973).

Spencer, Julia R., et al., "A Comparison of Endoscopic Suspension of the Vesical Neck With Suprapubic Vesicourethropexy for Treatment of Stress Urinary Incontinence" The Journal of Urology, vol. 137, pp. 411-415 (Mar. 1987).

Stamey, Thomas A., M.D., "Endoscopic Suspension of the Vesical Neck for Urinary Incontinence in Females" Ann Surg., vol. 192, No. 4, pp. 465-471 (Oct. 1980).

Stanton, Stuart L., FRCS, FRCOG, "Suprapubic Approaches for Stress Incontinence in Women" JAGS, vol. 38, No. 3, pp. 348-351 (1990), The American Geriatrics Society.

Staskin, David R., et al., "The Gore-tex sling procedure for female sphincteric incontinence: indications, technique, and results" World J Urol., vol. 15, pp. 295-299 (1997) Springer-Verlag.

Studdiford, William E., M.D., "Transplantation of Abdominal Fascia for the Relief of Urinary Stress Incontinence" Am J Obst Gynec, vol. 47, pp. 764-775 (1944) Bellevue Hospital and New York University College of Medicine.

Ulmsten, U., "Female Urinary Incontinence—A Symptom, Not a Urodynamic Disease. Some Theoretical and Practical Aspects on the Diagnosis and Treatment of Female Urinary Incontinence" The International Urogynecology Journal, vol. 6, pp. 2-3 (1995).

Ulmsten, U., et al., "A Multicenter Study of Tension-Free Vaginal Tape (TVT) for Surgical Treatment of Stress Urinary Incontinence" The International Urogynecology Journal, vol. 9, pp. 210-213 (1998).

Ulmsten, U., et al., "A three-year follow up of tension free vaginal tape for surgical treatment of female stress urinary incontinence" The British Journal of Obstetrics and Gynaecology, vol. 106, pp. 345-350 (Apr. 1999).

Ulmsten, U., et al., "An Ambulatory Surgical Procedure Under Local Anesthesia for Treatment of Female Urinary Incontinence" The International Urogynecology Journal, vol. 7, pp. 81-86 (1996).

Ulmsten, U., et al., "Different Biochemical Composition of Connective Tissue in Continent and Stress Incontinent Women" Acta Obstet Gynecol Scand, vol. 66, pp. 455-457 (1987).

Ulmsten, U., et al., "Intravaginal Slingplasty (IVS): An Ambulatory Surgical Procedure for Treatment of Female Urinary Incontinence" Scand J Urol Nephrol, vol. 29, pp. 75-82 (1995) Scandinavian University Press.

Ulmsten, U., et al., "The unstable female urethra" Am. J. Obstet. Gynecol., vol. 144 No. 1, pp. 93-97 (1982).

Walters, Mark D., Percutaneous Suburethral Slings: State of the Art Presented at the conference of the American Urogynecologic Society, Chicago, 29 pages (Oct. 2001).

Waxman, Steve et al., Advanced Urologic Surgery for Urinary Incontinence, The Female Patient, vol. 21, pp. 93-100 (Mar. 1996).

Webster, George D., "Female Urinary Incontinence" Urologic Surgery—3rd Ed., Ch. 66, pp. 665-679 (1983).

Webster, George D., et al., "Voiding Dysfunction Following Cystourethropexy: Its Evaluation and Management" The Journal of Urology, vol. 144, pp. 670-673 (Sep. 1990) American Urological Association, Inc.

Winter, Chester C., M.D., "Peripubic Urethropexy for Urinary Stress Incontinence in Women" Urology vol. XX, No. 4, pp. 408-411 (Oct. 1982).

Woodside, Jeffrey R., et al., "Suprapubic Endoscopic Vesical Neck Suspension for the Management of Urinary Incontinence in Myelodysplastic Girls" The Journal of Urology, vol. 135, pp. 97-99 (Jan. 1986).

Zacharin, Robert F., "The suspensory mechanism of the female urethra" Journal of Anatomy, vol. 97, Part 3, pp. 423-427, (1963).

Zacharin, Robert F., Frcs, Frcog, et al, "Pulsion Enterocele: Long-Term Results of an Abdominoperineal Technique" Obstetrics & Gynecology, vol. 55, No. 2, pp. 141-148 (Feb. 1980) The American College of Obstetricians & Gynecologists.

Zimmern, Phillippe E. et al., "Four-Corner Bladder Neck Suspension" Vaginal Surgery for the Urologist, vol. 2, No. 1, pp. 29-36 (Apr. 1994).

Declaration of Johann J. Neisz with Attachment (Mar. 19, 2004).

Bard, "Uretex Polypropylene Urethral Support—Safety, Simplicity, Flexibility" Marketing Material (2002) 8 pages.

Boston Scientific Corp., Boston Scientific Microvasive, "Precision Tack Transvaginal Anchor System—The Precise Approach to Transvaginal Sling Procedures" Marketing Material (1998) 4 pages.

Boston Scientific Corp., Boston Scientific Microvasive, "Precision Twist Transvaginal Anchor System—Low Profile Design for Precise Anchor Placement" Marketing Material (2000) 2 pages.

Boston Scientific Corp., "Advantage A/T—Surgical Mesh Sling Kit" Marketing Material (2002) 1 page.

Boston Scientific Corp., "Precision SpeedTac—Transvaginal Anchor System" Marketing Material (2002) 1 page.

Ethicon, Inc., TVT Tension-free Vaginal Tape, Gynecare, 23 pages (1999).

Gynecare TVT, "Tension-Free Support for Incontinence" Marketing Material, Gynecare Worldwide (Feb. 2002), 6 pages.

Gynecare, TVT—"Tension-Free Vaginal Tape, Minimally Invasive, Highly Effective Treatment for Female Stress Urinary Incontinence" Marketing Brochure, Ethicon, Inc. (1999) 6 pages.

Herniamesh USA Inc., "T-Sling (Totally Tension-free) Urinary Incontinence Procedure" Marketing Material (Jan. 2000), 2 pages.

Mentor, "The Strength of Suspend" Marketing Material (Mar. 2000) 6 pages.

Mentor, Sabre, "Generation Now" Marketing Material (May 2002) 4 pages.

Mentor, Sabre, Surgical Procedure, Marketing Material (Aug. 2002) 6 pages.

Mentor-Porges, Trans-obturator tape, Le hamac perinial, Nos references, Marketing Material in French language (2003) 1 page.

Porges U.K. Ltd., "Uratape Perineal Hammock Urethral Support Tape—New Generation of Tape Perineal Implantation" Mentor, Marketing Material (2002) 4 pages.

Safyre, "The Essence of a Contemporary Synthetic Sling—Self-Anchoring Complete Adjustability Elastic" Promedon, Marketing Material (Jan. 30, 2002) 4 pages.

Urogynecology, Product Catalog, eg. SIS Technology, Bladder Suspension, Urodynamics and Urinary Diversion, Incontinence, Cook, Urological Inc. (1996) 36 pages.

Dietz, Hans, MD, et al., "Does the tension-free vaginal tape stay where you put it?" Am. J. Obstet Gynecol. V. 188, No. 4, pp. 950-953 (2003).

Drutz, H., et al., "Clinical and Urodynamic Re-evaluation of Combined Abdominal Marlex Sling Operations for Recurrent Stress Urinary Incontinence" Int. Urogynecol J. 1: pp. 70-73 (1990).

Fianu, Stefan, et al, Absorbable Polyglactin Mesh for Retropubic Sling Operations in Female Urinary Stress Incontinence, Gyneol. Obstet. Invest. 16, pp. 45-50 (1983).

Mentor-Porges, Come See Us at Booth #28, Marketing Material (Jul. 2002) 1 page.

Mouly, Patrick, et al., "Vaginal Reconstruction of a Complete Vaginal Prolapse: The Trans Obturator Repair" Journal of Urology, Apr. 2003, vol. 169 (4) supplement, p. 183, Abstract # V 702, AUA (Apr. 26-May 1, 2003) Chicago, IL.

Nicita, G. et al. "Six Year Results of Prosthetic Vaginal Surgery for Cystocele Repair" European Urology Supplements 3 (2004) No. 2, p. 50 (Mar. 24-27, 2004).

Ogundipe, Anthony, MD, et al., "Modified Suburethral Sling Procedure for Treatment of Recurrent or Severe Stress Urinary Incontinence" Surg. Gynecol. Obstet., V175, pp. 173-176 (Aug. 1992).

"Safyre and Transobturator", Video file on CD-ROM (2004).

Timmons, M. Chrystie, et al., "Abdominal Sacral Colpopexy in 163 Women with Posthysterectomy Vaginal Vault Prolapse and Enterocele—Evolution of Operative Techniques" J. of Reproductive Medicine, V.35, No. 4, pp. 323-327 (Apr. 1992).

"Vesica Sling Kits with Press-In Percutaneous Anchor System—Simplifying Sling Procedures" Marketing Material, Boston Scientific Corp., Boston Scientific Microvasive, (1998), 4 pages.

Young, Stephen B., et al., "The Mersilene mesh suburethral sling: A clincal and urodynamic evaluation" Am. J. Obstet. Gynecol. V. 173, pp. 1719-1726 (Dec. 1995).

* cited by examiner

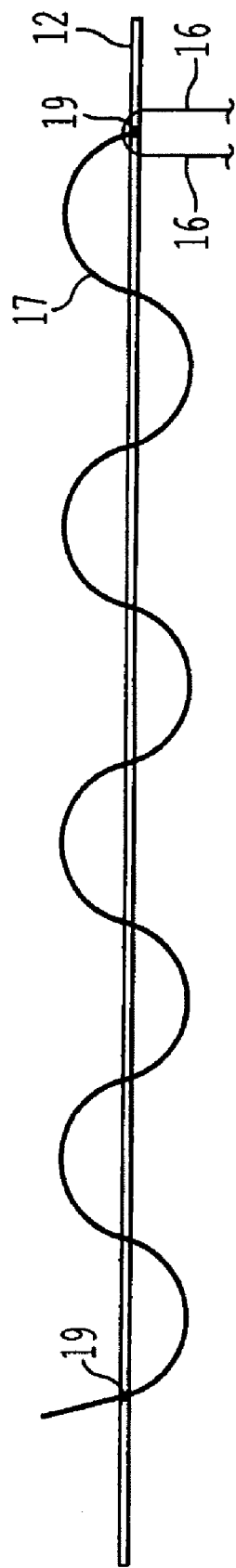
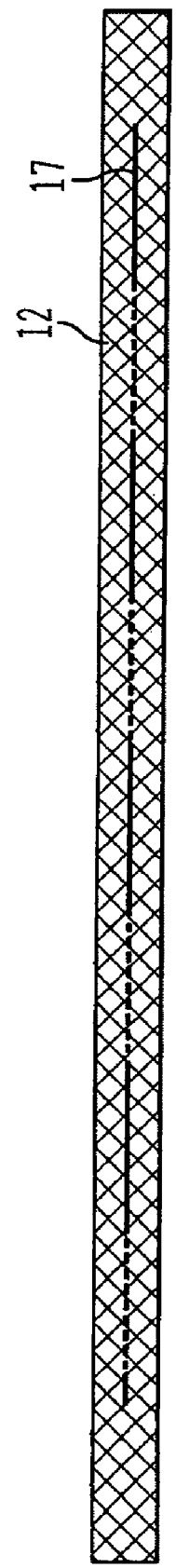
FIG. 3
FIG. 4

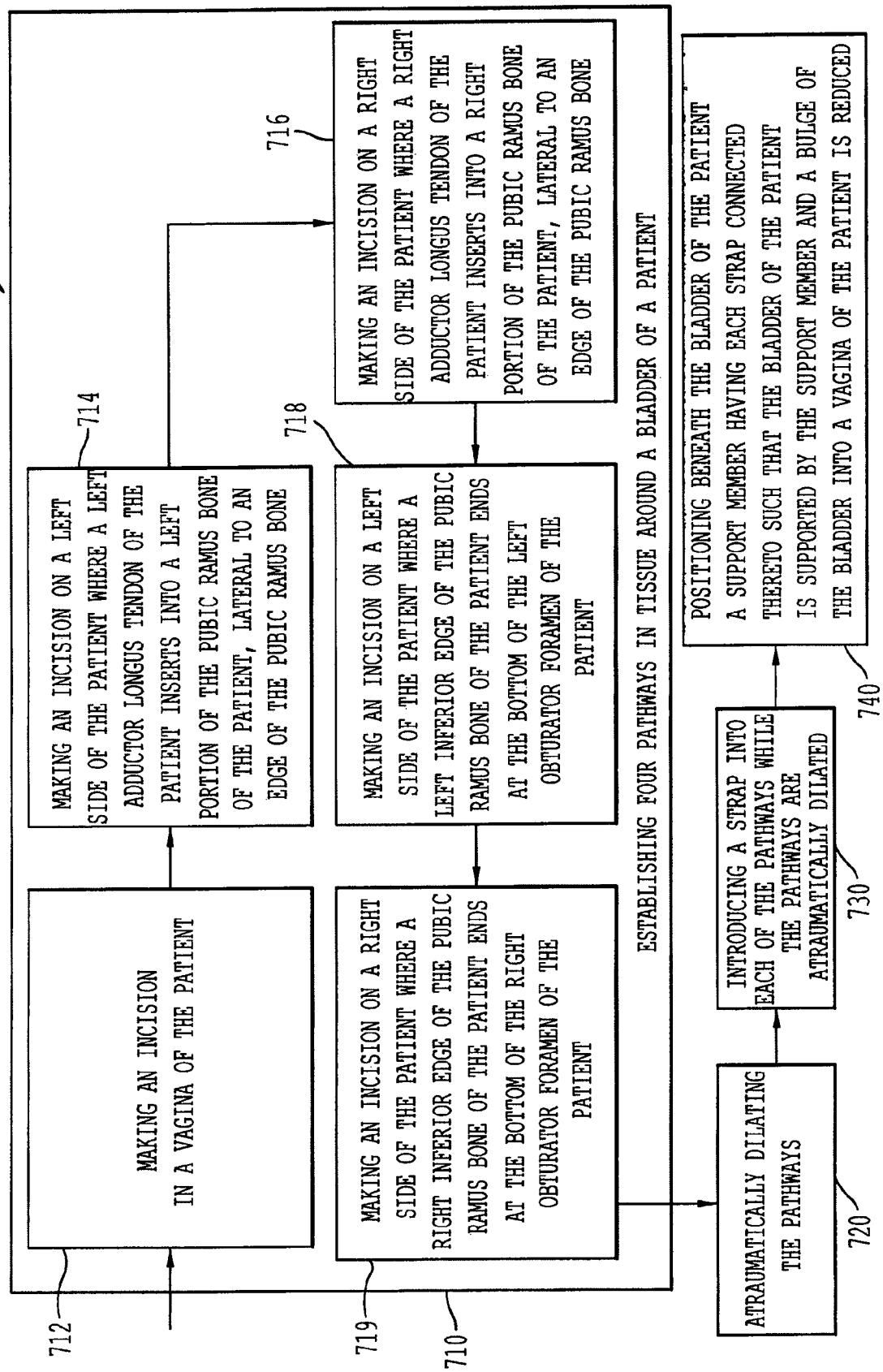

METHOD AND APPARATUS FOR CYSTOCELE REPAIR

CROSS-REFERENCE TO RELATED APPLICATIONS

This is a continuation of U.S. patent application Ser. No. 10/840,646, filed May 7, 2004.

BACKGROUND OF THE INVENTION

1. Field of the Invention

Urogenital Surgery

2. Description of the Related Art

Female genital prolapse has long plagued women. It is estimated by the U.S. National Center for Health Statistics that 247,000 operations for genital prolapse were performed in 1998. With the increasing age of the U.S. population, these problems will likely assume additional importance.

Vaginal prolapse develops when intra-abdominal pressure pushes the vagina outside the body. In a normal situation, the levator ani muscles close the pelvic floor. This results in little force being applied to the fasciae and ligaments that support the genital organs. Increases in abdominal pressure, failure of the muscles to keep the pelvic floor closed, and damage to the ligaments and fasciae all contribute to the development of prolapse.

Many techniques have been tried to correct or ameliorate the prolapse and its symptoms, with varying degrees of success. Nonsurgical treatment of prolapse involves measures to improve the factors associated with prolapse, including treating chronic cough, obesity, and constipation. Other nonsurgical treatments may include pelvic muscles exercises or supplementation with estrogen. These therapies may alleviate symptoms and prevent worsening, but the actual hernia will remain. Vaginal pessaries are the primary type of nonsurgical treatment, but there can be complications due to vaginal wall ulceration.

There is a desire to obtain a minimally invasive yet highly effective device and method that can be used to treat pelvic organ prolapse with minimal to no side effects. Such a device should reduce the complexity of the surgical procedure, be biocompatible, adjustable, and non-toxic. The treatment methods using the device should reduce pain, operative risks, infections and post operative hospital stays. Further, the method of treatment should also improve the quality of life for patients.

SUMMARY OF THE INVENTION

The present invention broadly provides a method and apparatus for cystocele repair. In one embodiment, the method includes the steps of: establishing four pathways in tissue around a bladder of a patient, introducing a strap into each of the pathways, and positioning beneath the bladder of the patient a support member having each of the straps connected thereto such that the bladder of the patient is supported by the support member. A bulge of the bladder into a vagina of the patient is reduced as a consequence of applying this method.

In another embodiment, an apparatus for repairing cystocele includes a support surface knitted with a first bar setting and a plurality of straps continuously knitted with the support member. The plurality of straps are knitted with a second bar setting.

In another embodiment, a kit for repairing cystocele includes a support apparatus including at least two straps, each of the straps including a connector configured to mate with a tip of a needle. The kit further includes a first needle configured to extend from an incision on the left side of the patient where a left inferior edge of the pubic ramus bone of the patient ends at the bottom of the left obturator foramen of the patient, through the left obturator foramen of the patient, to an incision in the vagina of the patient; and a second needle configured to extend from an incision on the right side of the patient where a right inferior edge of the pubic ramus bone of the patient ends at the bottom of the right obturator foramen of the patient, through the right obturator foramen of the patient, to the incision in the vagina of the patient.

In another embodiment, a surgical implant kit includes a support apparatus including at least two straps, each of the straps comprising a connector configured to mate with a tip of a needle. Each connector has an aperture configured to receive the tip of the needle. Each aperture has a different shape. The kit further includes at least two needles, each needle having a tip having a shape configured to mate with one aperture of the at least two connectors.

In another embodiment, a surgical implant kit includes a support apparatus including at least two straps, each of the straps including a connector configured to mate with a tip of a needle. Each connector has identifying indicia thereon. The kit further includes at least two needles.

In another embodiment, a surgical implant kit includes a support apparatus including at least two straps, each of the straps including a connector configured to mate with a tip of a needle. Each connector has a color. The kit further includes at least two needles, each needle having a handle and each handle having a color matching a color of a corresponding connector.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3 is a side view of a strap of a support apparatus of the present invention;

FIG. 4 is a top view of a front view of a strap of a support apparatus of the present invention;

FIG. 8A is a side view of a support member including both a biologic graft and a synthetic support member;

FIG. 41 is a flow chart illustrating an alternate method of practicing the present invention.

DETAILED DESCRIPTION OF THE PREFERRED EMBODIMENTS

Figure 1:
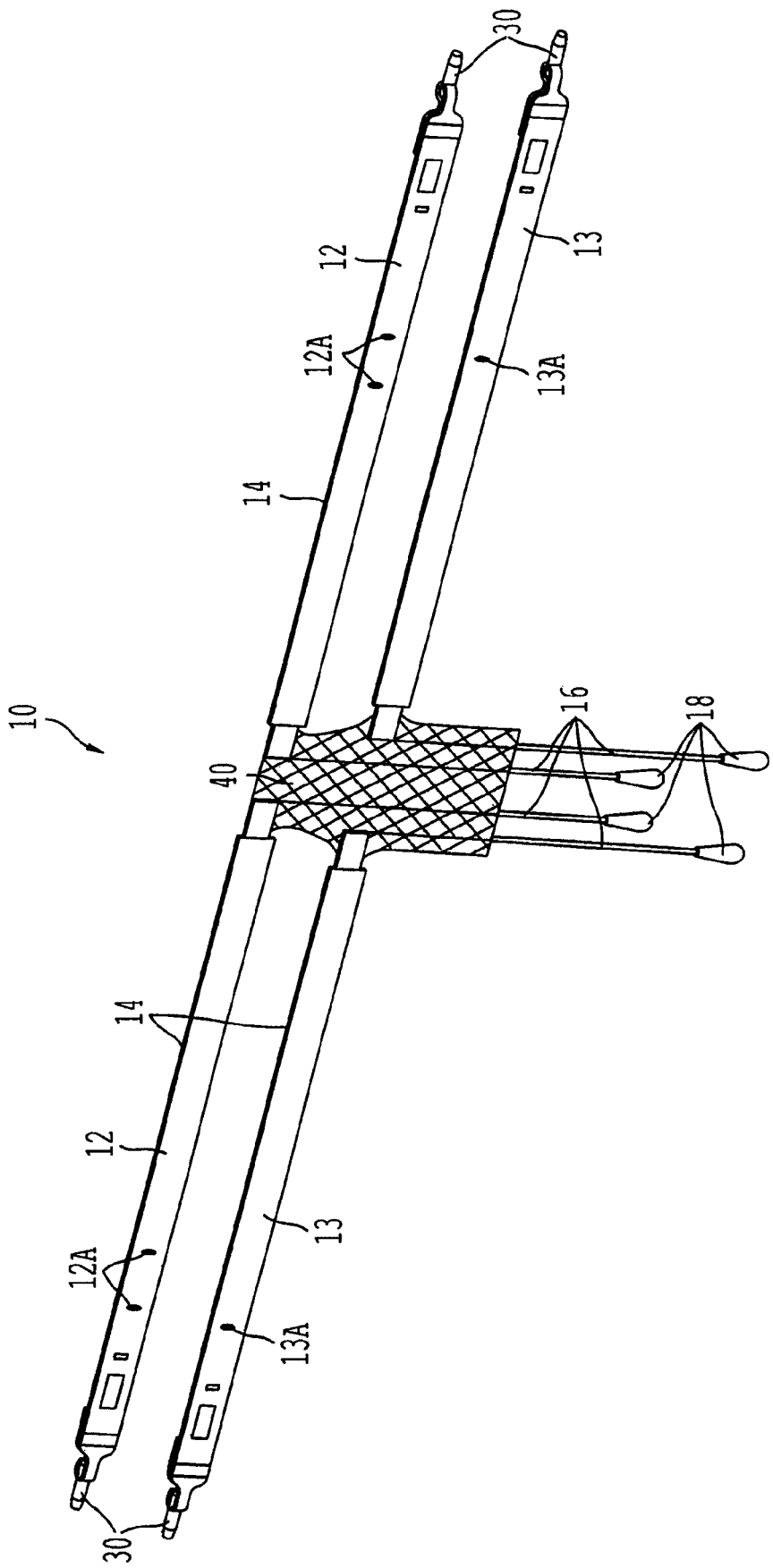
FIG. 1 is a perspective view of a first embodiment of a support apparatus of the present invention.

Referring now to the drawings, wherein like reference numerals designate identical or corresponding parts throughout the several views.

Figure 2:
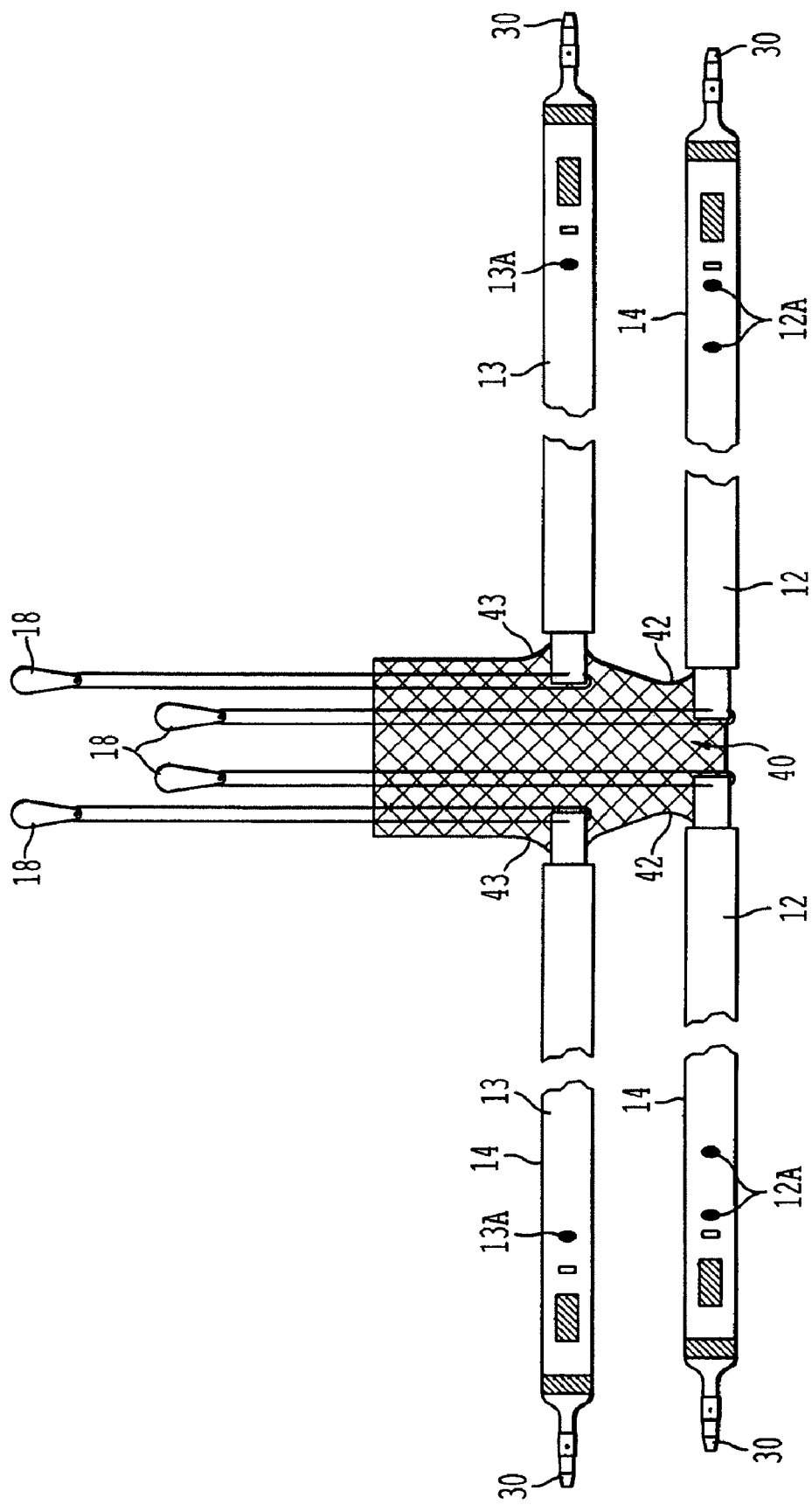
FIG. 2 is a fragmentary front view of a first embodiment of the support apparatus.

FIGS. 1 and 2 illustrate a surgical support apparatus 10 of a first embodiment of the present invention. The apparatus 10 is configured to be surgically implanted in a female patient to repair anterior prolapse of the vagina. The present invention may be used to correct central defects, midline defects, or both midline and central defects at once. In the embodiment shown in FIGS. 1 and 2, apparatus 10 comprises two superior straps 12, two inferior straps 13, a support member 40, and four loosening sutures 16. Each of straps 12 and 13 include a connector 30. Each strap 12 and 13 is covered by a sheath 14. Each suture 16 includes a tab 18. Straps 12 and 13 are connected to tabs 42 and 43 of support member 40 by known means.

In one embodiment, sheath 14 is made of polyethylene. Other material may be used, such as polypropylene, nylon, polyester, or Teflon. The sheath is configured to be removed from the strap after the strap is in the correct position in the body.

In one embodiment, straps 12 and 13 are 19.69 inches long and 0.433 inches wide. The straps are 0.024 inches thick. Straps 12 and 13 are knitted of 4 or 6 mil polypropylene monofilament and are heat set at 280-300 degrees Fahrenheit for 5-8 minutes. Also, in one embodiment, support member 40 is 10 cm long by 5 cm wide and 0.021 inches thick. Member 40 is knitted of 4 mil polypropylene monofilament and heat set at 310-330 degrees Fahrenheit for 5-8 minutes. Both the strap and support member have a stitch count of 27.5 courses/inch (±2 courses) and 13 wales/inch (±2 wales).

In one embodiment, the straps are knitted with bar settings of: Bar 1: 1/0, 2/1 and Bar 2: 0/1, 1/2. The support member is a large pore mesh, knitted with bar settings of: Bar 1: 1/0, 2/3, 2/1, 2/3, 1/0, 1/2, 1/0, 1/2; Bar 2: 1/0, 2/3, 2/3, 1/0; and Bar 3: 2/3, 1/0, 1/2, 1/0, 2/3, 2/1, 2/3, 2/1. The straps are connected to the support member after knitting. Weaving according to a given bar pattern is described, for example, in "Warp Knitting Production" by Dr. S. Raz, Melliand Textilberichte GmbH, Rohrbacher Str. 76, D-6900 Heidelberg, Germany (1987), the contents of which are incorporated by reference herein.

Straps 12 and 13 and or sheaths 14 may also include indicia thereon to signify the correct orientation for implantation into a patient. In the embodiment shown in FIGS. 1 and 2, sheaths 14 around straps 12 include indicia 12A to show that straps 12 are the superior straps, and sheaths 14 around straps 13 include indicia 13A to show that straps 13 are the inferior straps. Words, symbols, and colors are all possible indicia that may be used, and these modifications are intended to be within the spirit and scope of the invention as claimed. Further, the indicia may be located on the straps, the sheaths, or both.

Apparatus 10 includes dilating connectors 30. Suitable dilating connectors are disclosed in Published U.S. Patent Application Serial Nos. 2002/151762 and 2002/147382 and U.S. patent application Ser. No. 10/386,897, filed Mar. 11, 2003.

Support member 40 is sized and shaped to afford repair of a cystocele without lifting the patient's bladder and without placing undue tension on the bladder or vaginal wall. The shape of member 40 may be predetermined, or the member may be trimmed based on patient anatomy before implantation.

FIGS. 3 and 4 illustrate an embodiment of a strap for a surgical apparatus of the present invention. In one embodiment, strap 12 includes tensioning suture 17. Tensioning suture 17 passes through the mesh of strap 12 multiple times, as shown in FIGS. 3 and 4. Tensioning suture 17 is affixed to strap 12 at points 19, to allow transfer of tension from the suture to the strap. In one embodiment, tensioning sutures are included in all the straps of the support apparatus. It should be readily apparent to one skilled in the art that other configurations of tensioning sutures and attachment points to a mesh strap are possible, and these modifications are within the scope of the invention as claimed.

Tensioning suture 17 is configured to eliminate slack in a strap that is already surgically implanted in the body. By tightening the strap with suture 17, rather than pulling on the strap itself, the surgeon prevents damage to the strap due to deformation. Damage to surrounding tissues due to excessive movement of the strap during adjustment is also avoided. Straps including tensioning sutures are disclosed in copending U.S. patent application Ser. No. 10/616,925, incorporated by reference herein.

Strap 12 also includes a connection point for loosening suture 16. As discussed below, loosening suture 16 is pulled by the surgeon to loosen the installed support member, if necessary.

Figure 5:
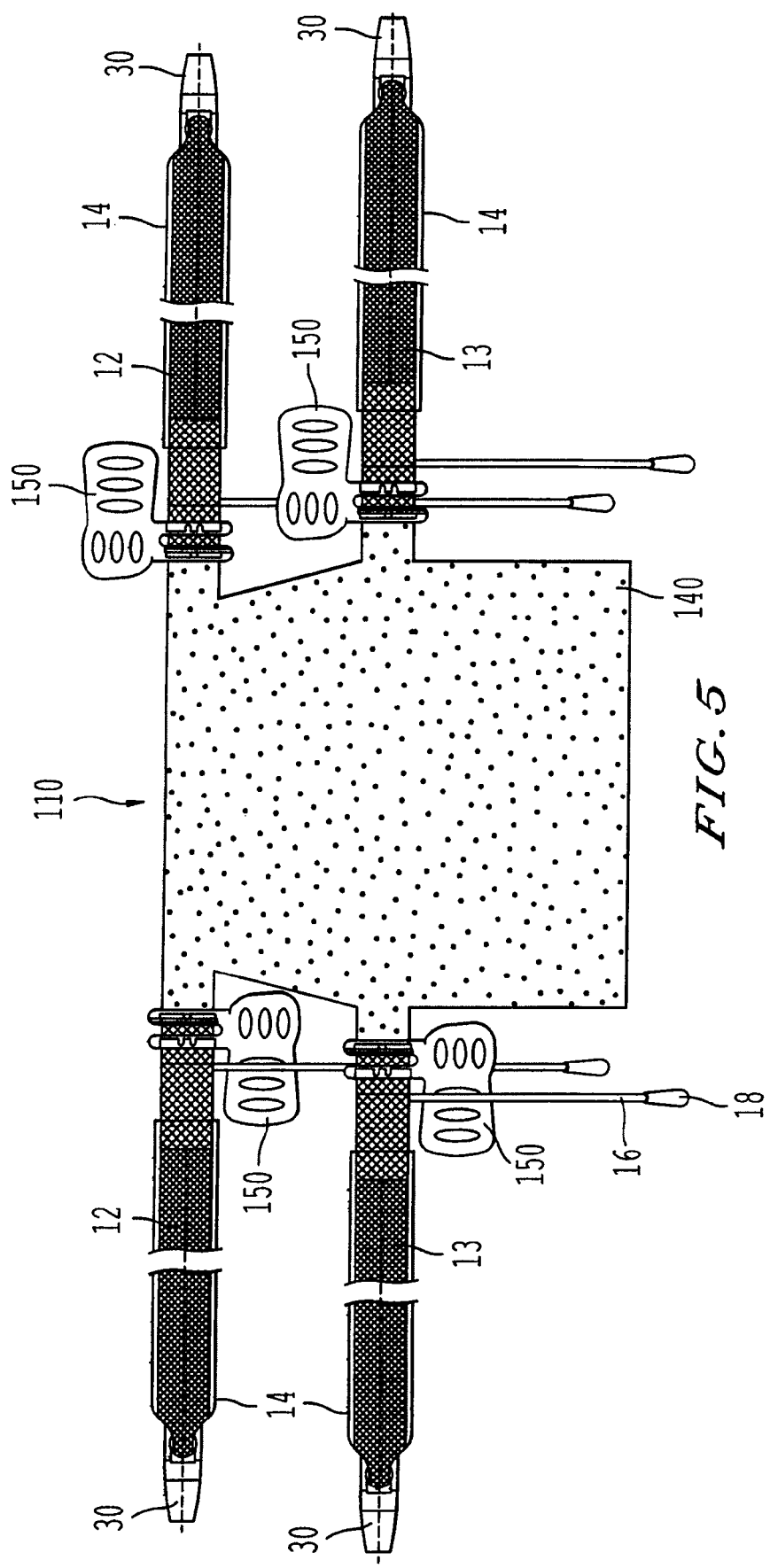
FIG. 5 is a fragmentary front view of a second embodiment of a support apparatus of the present invention.

FIG. 5 illustrates a second embodiment of the surgical support apparatus of the present invention. Apparatus 110 includes a biological graft for a support member 140. To attach the graft to straps 12 and 13, clamps 150 are used to hold the surfaces of the strap and member together. The surfaces are then secured together, as discussed below in the method for preparing the biologic graft. Straps 12 and 13, sheaths 14, and connectors 30 are described above.

In another embodiment, biologic graft comes in a kit already secured to straps 12 and 13. In this case, the preparation method below is unnecessary.

Figure 6:
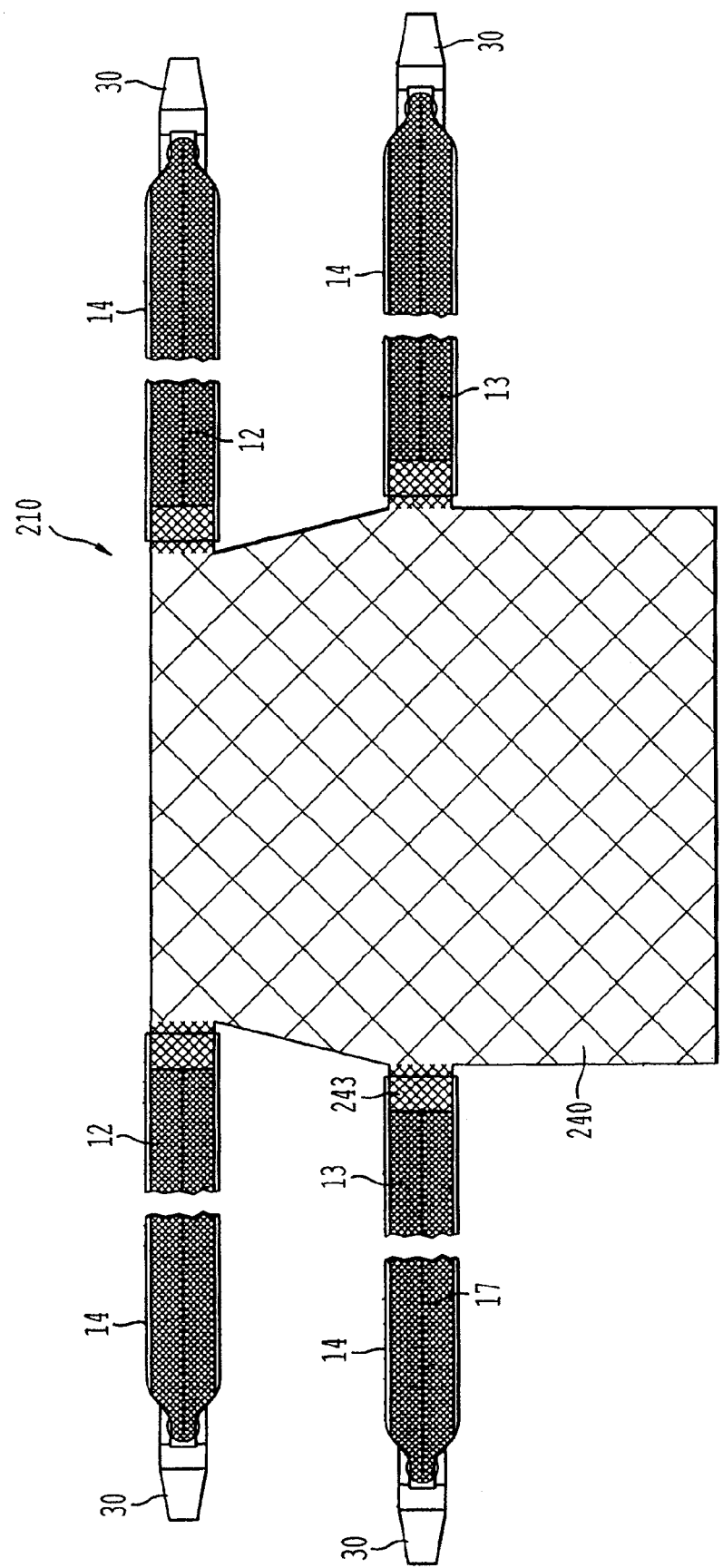
FIG. 6 is a fragmentary front view of a third embodiment of a support apparatus of the present invention.

FIG. 6 shows a third embodiment of the surgical support apparatus of the present invention. Apparatus 210 includes straps 12 and 13, sheaths 14, and support member 240. In this embodiment, support member 240 and straps 12 and 13 are continuously knitted. Thus, there is no seam between the straps and support member, as they are one continuous piece. This results in a thinner transition area 243 from the straps to the support member, which results in a less bulky apparatus for installment into the patient. An apparatus that is less bulky will be less likely to abrade the surrounding tissue.

The support member is knitted with a first bar pattern, and the straps are knitted with a second bar pattern. This allows larger pores in the support member, creating a support member that is more flexible and more likely to allow tissue ingrowth. A second bar pattern for the straps allows a smaller pore size for the straps, creating a strap that can carry a larger load with a smaller, less intrusive strap width.

In one embodiment, the straps and support member are continuously knitted of 4 mil polypropylene monofilaments, knitted with a warp tricot. The stitch count is 27.5 courses/inch (±2 courses) and 13 wales/inch (±2 wales). The support member is a large pore mesh, with bar settings of: Bar 1: 1/0, 2/3, 2/1, 2/3, 1/0, 1/2, 1/0, 1/2; Bar 2: 1/0, 2/3, 2/3, 1/0; and Bar 3: 2/3, 1/0, 1/2, 1/0, 2/3, 2/1, 2/3, 2/1. The thickness of the support member is about 0.21 inches.

Figure 7:
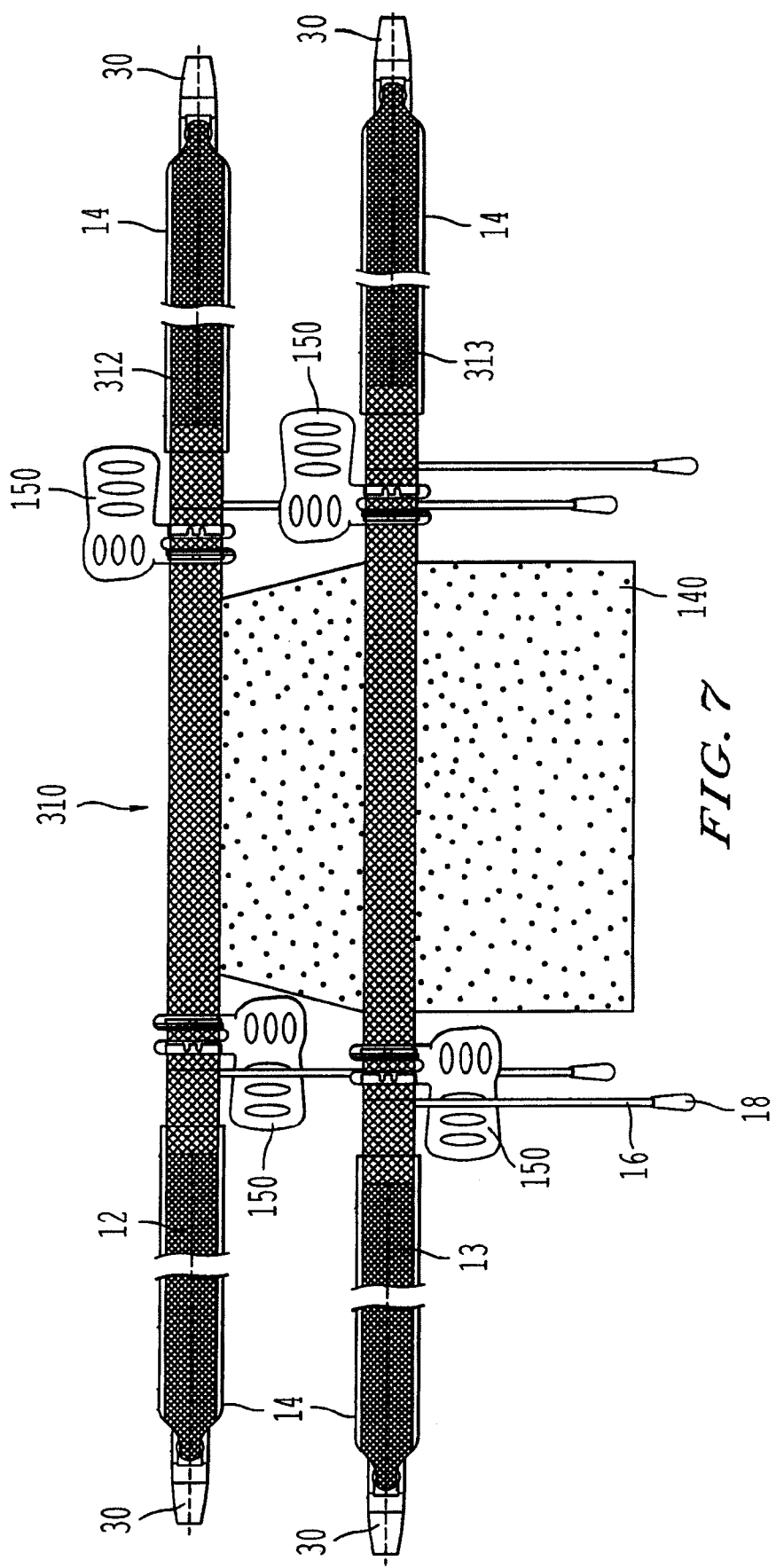
FIG. 7 is a front view of a biologic graft attached to a central portion of two straps, each strap having a connector at each end.

FIG. 7 shows an alternate embodiment of the surgical apparatus of the present invention. Apparatus 310 includes straps 312 and 313 and biologic graft 140. Straps 12 and 13 have connectors 30 at each end thereof. Biologic graft 140 is connected to a central portion of each strap. In the embodiment shown in FIG. 7, biologic graft 140 is connected to strap 12 and strap 13 at a portion equidistant from each end of the straps. It should be readily apparent to one skilled in the art that other configurations are possible, and these modifications are within the scope of the invention as claimed.

Figure 8:
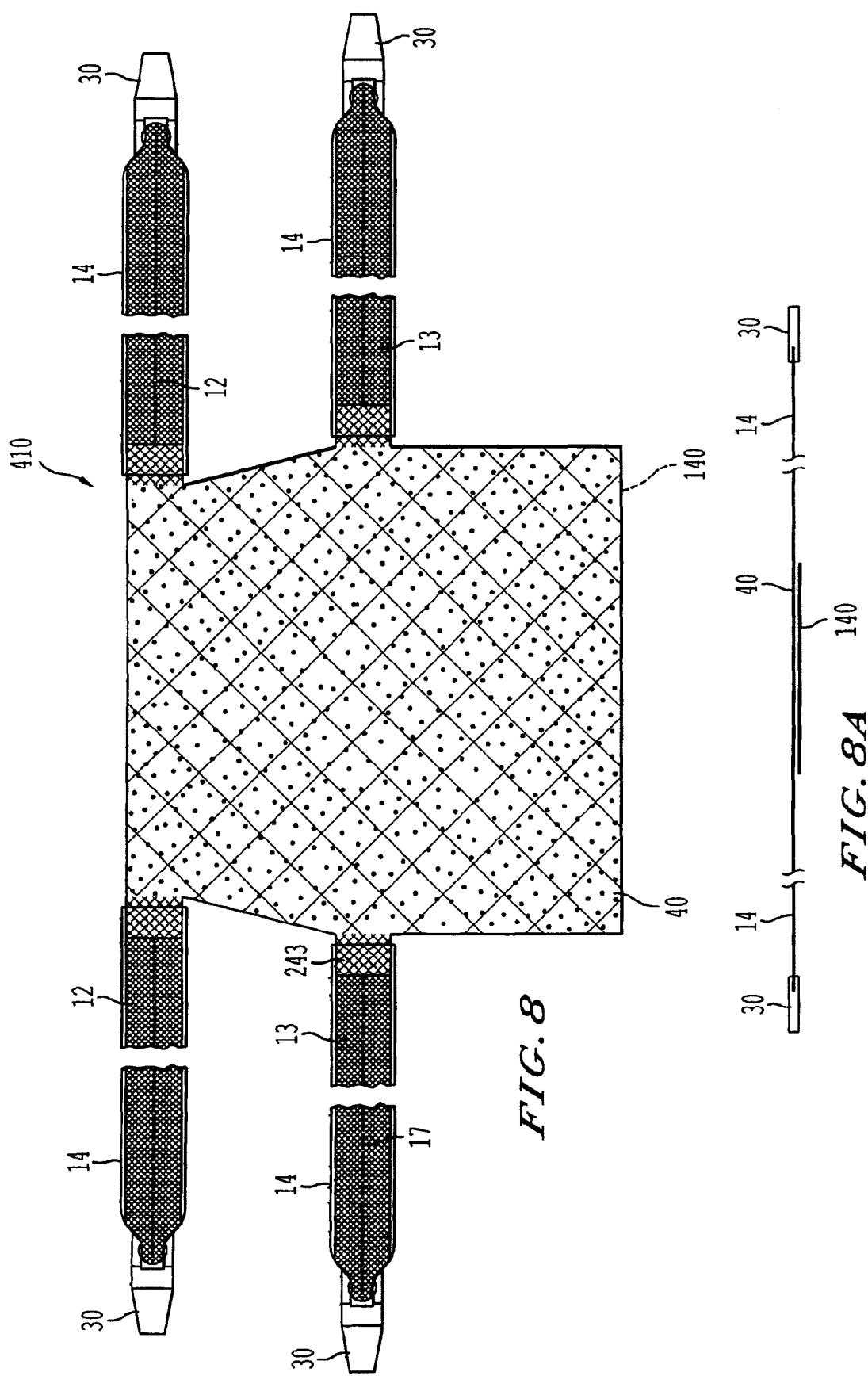
FIG. 8 is a front view of a support member including both a biologic graft and a synthetic support member.

FIGS. 8 and 8A illustrate a surgical apparatus according to another alternate embodiment of the present invention. Apparatus 410 includes a biologic graft 140 and a synthetic support member 40. In the embodiment shown in FIGS. 8 and 8A, biologic graft 140 and synthetic support member 40 have the same area and are attached to overlie one another. However, it should be readily apparent to one skilled in the art that a surgical support apparatus having a biologic graft and a synthetic support member having different areas and/or offset from one another could be used, and these modifications are within the scope of the invention as claimed. Further, apparatus 410 may be implanted in the patient such that biologic graft 140 faces the bladder and support member 40 faces the vaginal wall, or such that biologic graft 140 faces the vaginal wall and support member 40 faces the bladder. The implantation configuration is based on the preference of the surgeon.

Figure 9:
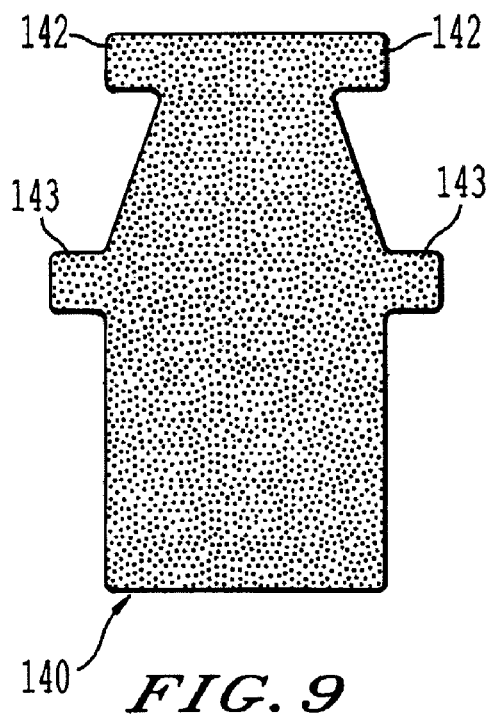
FIG. 9 is a front view of a support member of the second embodiment of the support apparatus.

FIG. 9 shows support member 140 made of a non-synthetic material. Suitable non-synthetic materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium and fascia lata. Member 140 includes tabs 142 and 143 for connecting to straps, as shown in FIG. 5.

Figure 10:
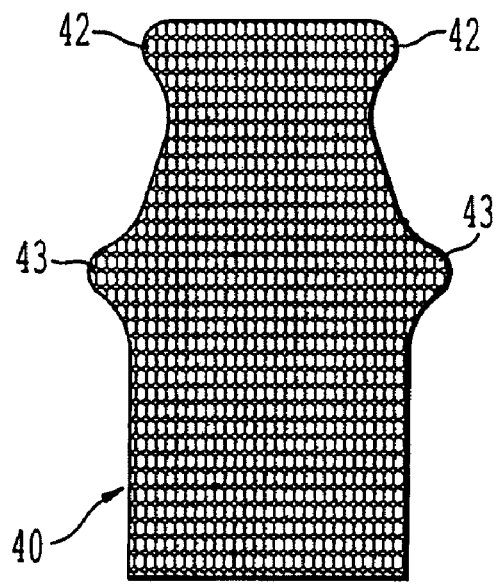
FIG. 10 is a front view of a support member of the first embodiment of the support apparatus.

FIG. 10 shows support member 40 made of a synthetic material. Member 40 includes tabs 42 and 43 for connecting to straps, as shown in FIG. 1. Commercial examples of synthetic materials include Marlex™ (polypropylene) available from Bard of Covington, R. I., Prolene™ (polypropylene), Prolene Soft Polypropylene Mesh or Gynemesh (nonabsorbable synthetic surgical mesh), both available from Ethicon, of New Jersey, and Mersilene (polyethylene terphthalate) Hernia Mesh also available from Ethicon, Gore-Tex™ (expanded polytetrafluoroethylene) available from W. L. Gore and Associates, Phoenix, Ariz., and the polypropylene sling available in the SPARC™ sling system, available from American Medical Systems, Inc. of Minnetonka, Minn., Dexon™ (polyglycolic acid) available from Davis and Geck of Danbury, Conn., and Vicry™ available from Ethicon.

Other examples of suitable materials include those disclosed in published U.S. patent application Ser. No. 2002/0072694. More specific examples of synthetic materials include, but are not limited to, polypropylene, cellulose, polyvinyl, silicone, polytetrafluoroethylene, polygalactin, Silastic, carbon-fiber, polyethylene, nylon, polyester (e.g. Dacron) polyanhydrides, polycaprolactone, polyglycolic acid, poly-L-lactic acid, poly-D-L-lactic acid and polyphosphate esters. See Cervigni et al., *The Use of Synthetics in the Treatment of Pelvic Organ Prolapse*, Current Opinion in Urology (2001), 11: 429-435.

Figure 11:
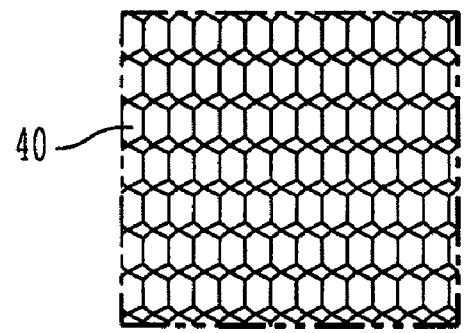
FIG. 11 is a close up view of the weave pattern of an embodiment of the support apparatus.
Figure 11A:
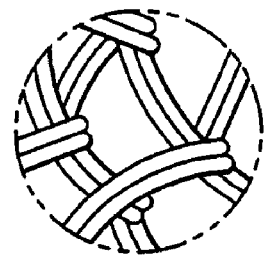
FIG. 11A is a close up view of an alternate weave pattern for the support member.

FIGS. 11 and 11A illustrate two possible embodiments for the stitching of synthetic support member 40. However, it should be readily apparent to one skilled in the art that other knitting patterns are possible, and these modifications are within the scope of the invention as claimed.

Figure 12:
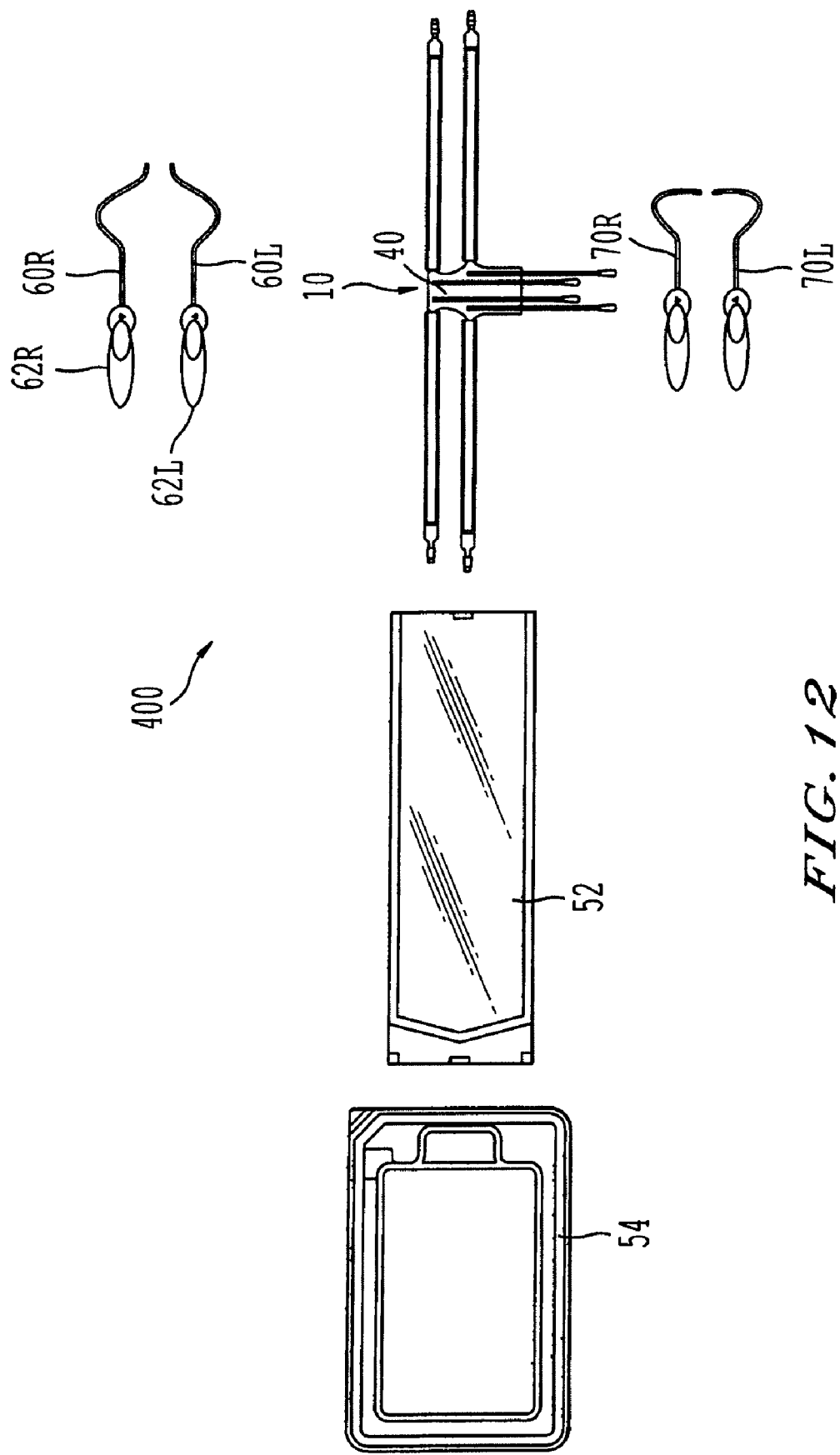
FIG. 12 is a front view of a surgical kit of an embodiment of the present invention.
Figure 13:
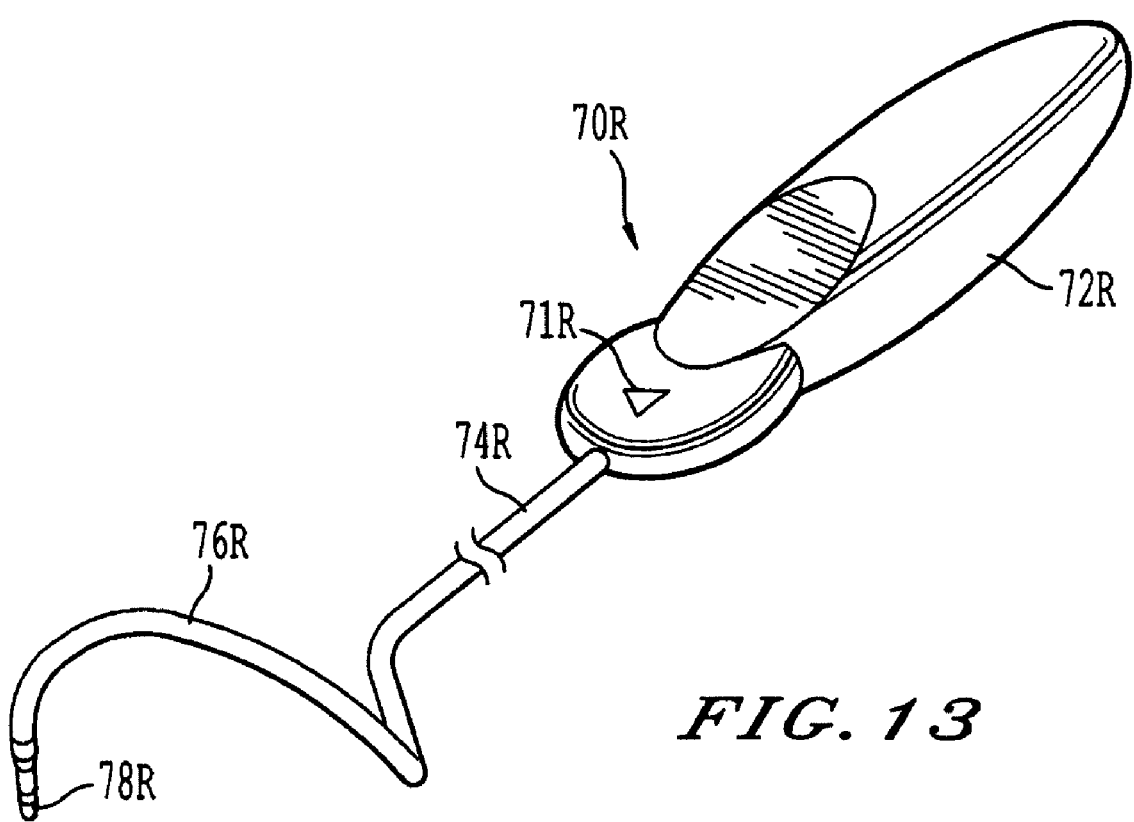
FIG. 13 is a perspective view of an embodiment of a right superior needle (the superior needle held in the surgeon's right hand) of the present invention.
Figure 14:
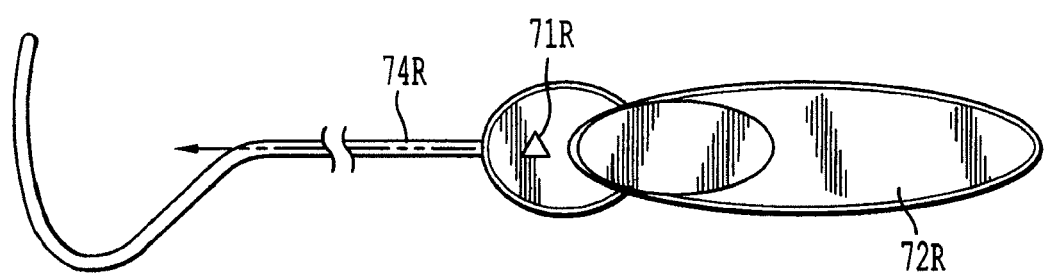
FIG. 14 is a top view of an embodiment of the right superior needle of the present invention.
Figure 15:
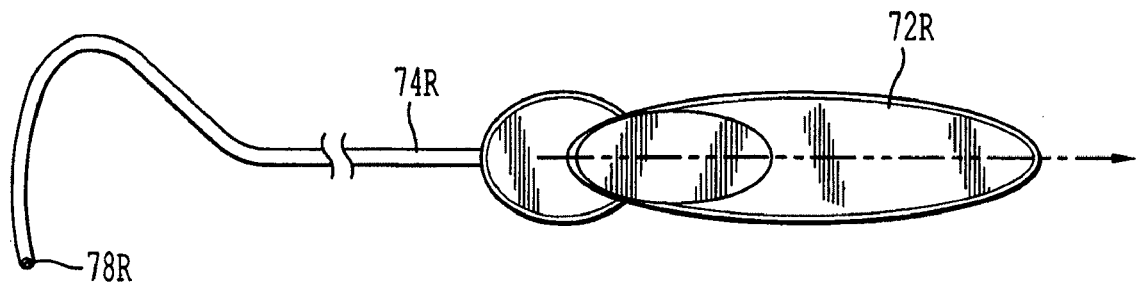
FIG. 15 is a bottom view of an embodiment of the right superior needle of the present invention.
Figure 16:
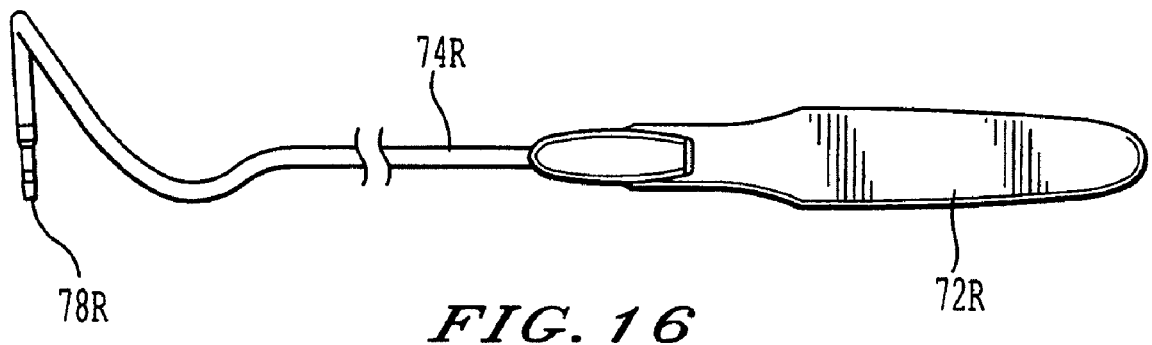
FIG. 16 is a left side view of an embodiment of the right superior needle of the present invention.
Figure 17:
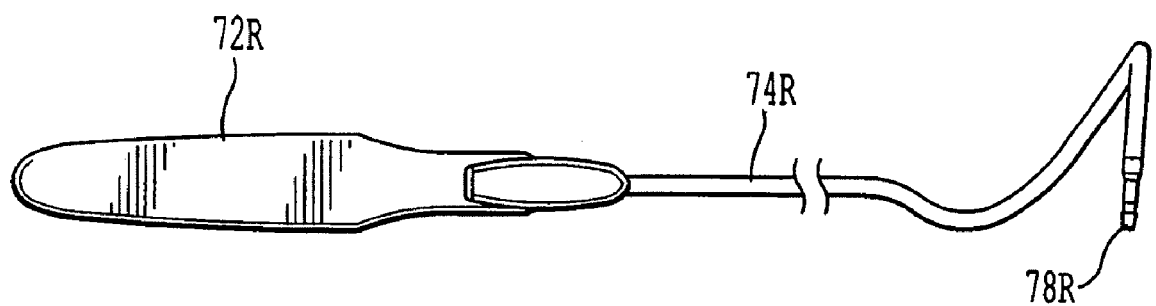
FIG. 17 is a right side view of an embodiment of the right superior needle of the present invention.
Figure 18:
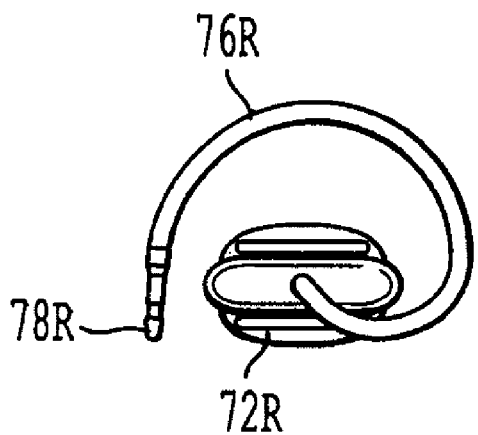
FIG. 18 is a front view of an embodiment of the right superior needle of the present invention.
Figure 19:
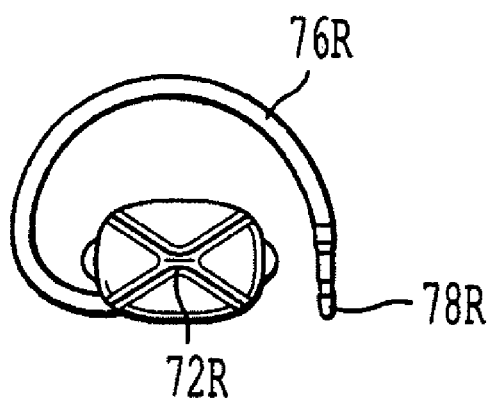
FIG. 19 is a rear view of an embodiment of the right superior needle of the present invention.
Figure 20:
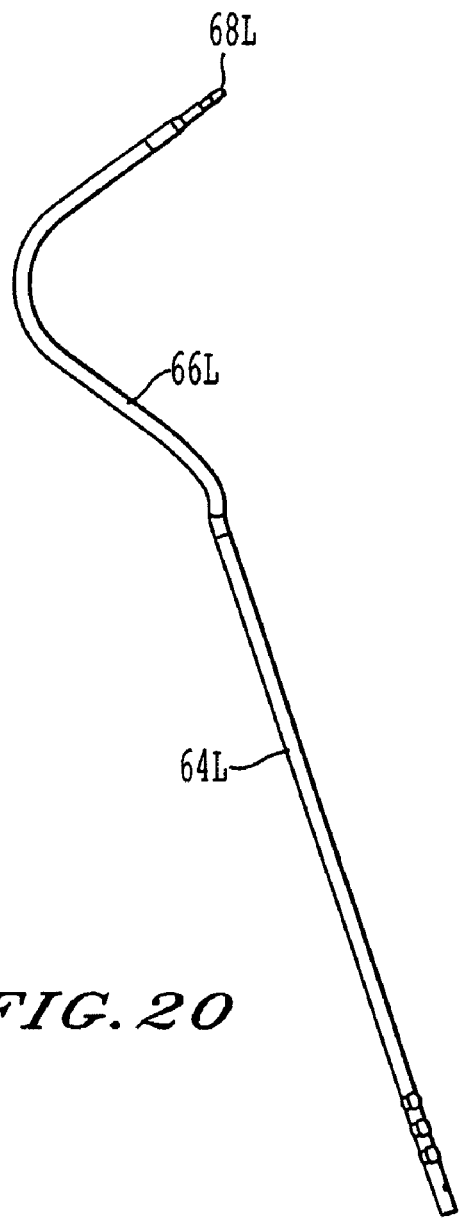
FIG. 20 is a side perspective view of an embodiment of a left inferior needle shaft of the present invention, without a handle.
Figure 21:
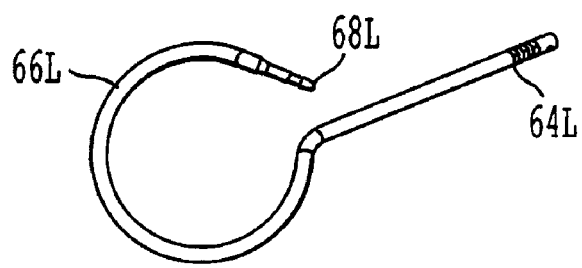
FIG. 21 is a front perspective view of an embodiment of the left inferior needle shaft of the present invention, without a handle.
Figure 22:
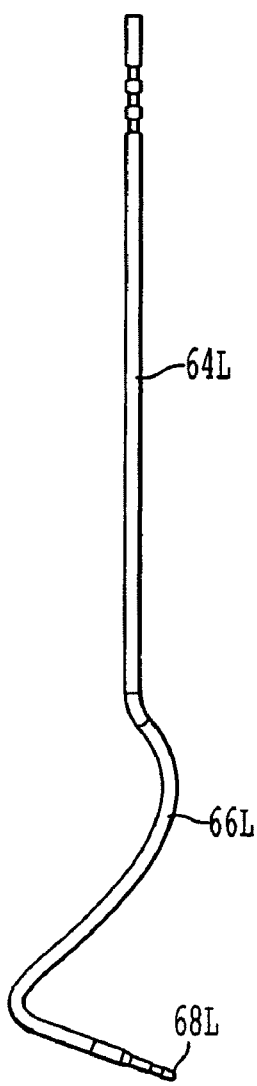
FIG. 22 is a right side view of an embodiment of a left inferior needle shaft of the present invention, without a handle.
Figure 23:
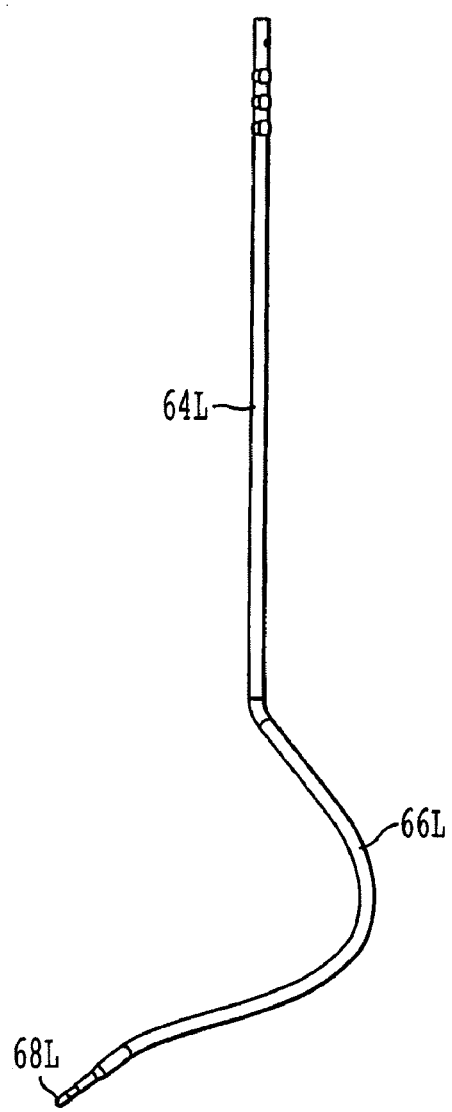
FIG. 23 is a bottom view of an embodiment of the left inferior needle shaft of the present invention, without a handle.
Figure 24:
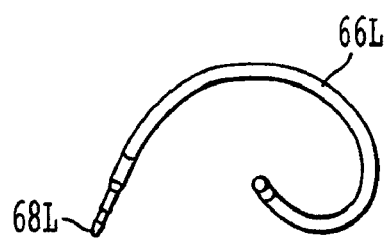
FIG. 24 is a front view of an embodiment of the left inferior needle shaft of the present invention, without a handle.

Referring to FIG. 12, in another aspect, the present invention includes a surgical kit 400. The kit 400 preferably includes at least two superior needles 70R and 70L. Right superior needle 70R is configured to be held in the surgeon's right hand and such that the tip of the needle enters an incision on the left side of the patient where the left adductor longus tendon of the patient inserts into a left portion of the pubic ramus bone of the patient, lateral to the edge of the pubic ramus bone, and travels through the top of the left obturator foramen to exit through an incision in the vagina of the patient. Left superior needle 70L is configured to be held in the surgeon's left hand and such that the tip of the needle enters an incision on the right side of the patient where the right adductor longus tendon of the patient inserts into a right portion of the pubic ramus bone of the patient, lateral to the edge of the pubic ramus bone, and travels through the top of the right obturator foramen to exit through an incision in the vagina of the patient.

In various embodiments of the present invention, the kits may further include the needles described in published U.S. patent application Ser. Nos. 20023-0065246-A1; 2002-0151762-A1; 2002-0147382-A1; 2002-0107430-A1, U.S. patent application Ser. No. 2002-0099258-A1 and U.S. patent application Ser. No. 2002-0099259-A1; and U.S. Provisional Application Ser. Nos. 60/263,472, filed Jan. 23, 2001; 60/269,829, filed Feb. 20, 2001; 60/281,350, filed Apr. 4, 2001; 60/295,068, filed Jun. 1, 2001; 60/306,915, filed Jul. 20, 2001, and 60/332,330, filed Nov. 20, 2001. In an embodiment that is particularly suitable for a transobturator surgical procedure, the needles include needles as described in U.S. patent application Ser. No. 10/306,179 filed Nov. 27, 2002.

The individual elements of the kits of the present invention may be packaged together as shown in FIG. 12 with a cover 52 and tray 54. Alternatively, the individual elements may be separately packaged or packaged in subassemblies depending on a variety of factors such as shelf life and sterilization requirements. They may be assembled at the manufacturing location or at the healthcare location. Any suitable sterilization procedure may be utilized to sterilize the contents of a kit. Suitable sterilization techniques include, but are not limited to, steam, ethylene oxide, electron beam, vapor (e.g. hydrogen peroxide or peracetic acid), gamma or plasma procedures.

The kit shown in FIG. 12 includes a support apparatus including a mesh support member 40. It should be readily apparent to one skilled in the art that kits using biological support members, as described above, may be made, and these modifications are within the scope of the invention as claimed. Further, a kit comprising a biologic graft may have the biologic graft pre-attached to the straps, or the graft may be separate from the straps and require the surgeon to attach the straps to the graft, as discussed below.

The kit shown in FIG. 12 also includes four needles: right inferior needle 60R, left inferior needle 60L, right superior needle 70R, and left superior needle 70L. Embodiments of these needles are shown in FIGS. 13-24 and are described herebelow.

FIGS. 13-19 illustrate an embodiment of right superior needle 70R of the present invention. (Left superior needle 70L is a mirror image of the right superior needle 70R.) Right superior needle 70R includes indicia 71R, handle 72R, shaft 74R, curved portion 76R, and tip portion 78R. Indicia 71R designates whether the needle is the right or left needle by pointing to the surgeon's right or left side, as the surgeon holds the needle handle. (The surgeon's right side corresponds to the patient's left side.)

Figure 38:
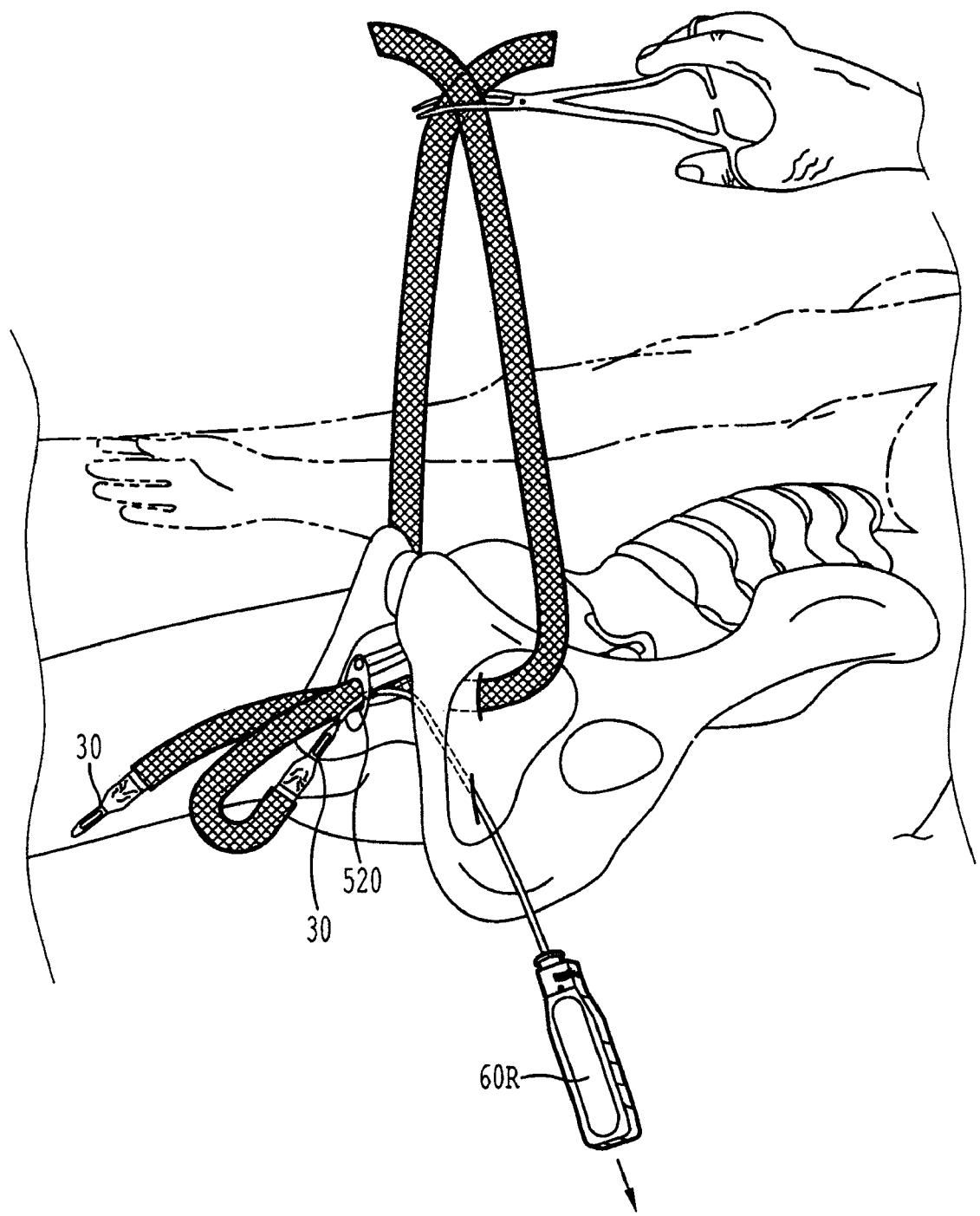
FIG. 38 is a perspective view of a right inferior needle tip exiting the vaginal incision.

FIGS. 20-24 illustrate an exemplary shaft of left inferior needle 60L, without handle 62L. (Right inferior needle 60R is a mirror image of the left inferior needle 60L.) Left inferior needle 60L includes a handle 62L, a shaft 64L, a curved portion 66L, and a tip portion 68L. Left inferior needle 60L is configured to be held in a surgeon's left hand such that tip 68L enters an incision 530L on the right side of the patient where a right inferior edge of the pubic ramus bone of the patient ends at a bottom of the right obturator foramen of the patient, and travels through the right obturator foramen to exit through an incision in the vagina of the patient. Right inferior needle 60R is configured to be held in a surgeon's right hand such that tip 68R enters an incision on the left side of the patient where a left inferior edge of the pubic ramus bone of the patient ends at a bottom of the left obturator foramen of the patient, and travels through the left obturator foramen to exit through an incision in the vagina of the patient. This is shown in FIG. 38.

The above-described needles may be disposable or reusable.

Figure 25:
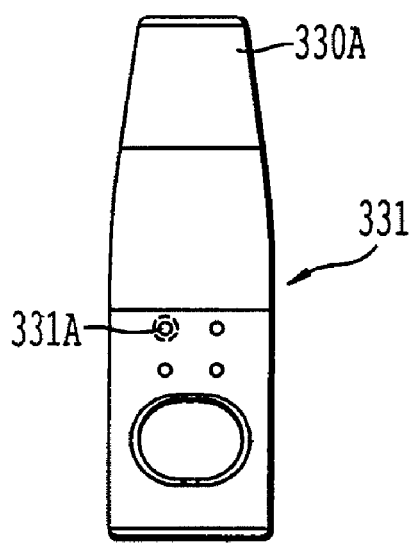
FIG. 25 is a front view of an embodiment of a left superior strap connector having symbolic indicia thereon.
Figure 26:
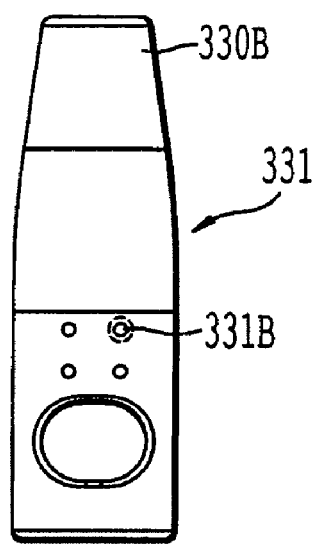
FIG. 26 is a front view of an embodiment of a right superior strap connector having symbolic indicia thereon.
Figure 27:
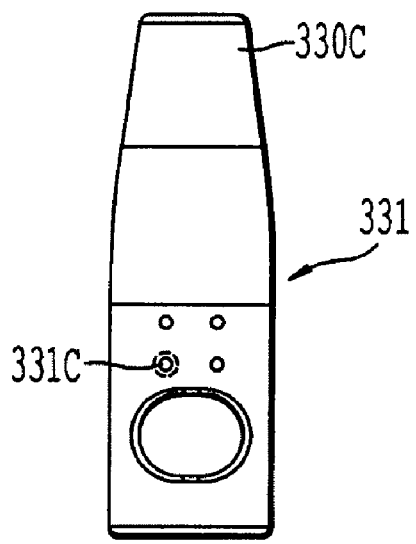
FIG. 27 is a front view of an embodiment of a left inferior strap connector having symbolic indicia thereon.
Figure 28:
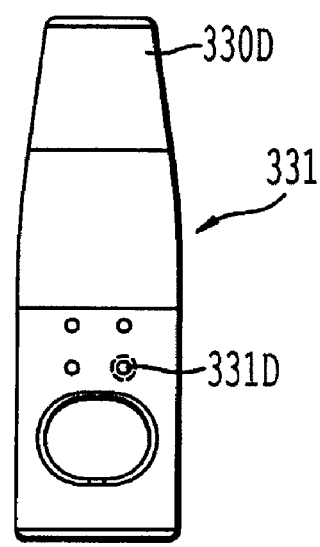
FIG. 28 is a front view of an embodiment of a right inferior strap connector having symbolic indicia thereon.

FIGS. 25-28 show connectors of the present invention having indicia thereon. FIG. 25 shows left superior connector 330A having indicia 331. Indicia 331 includes symbol 331A indicating that the connector is the left superior connector. FIG. 26 shows right superior connector 330B having indicia 331. Indicia 331 includes symbol 331B indicating that the connector is the right superior connector. FIG. 27 shows left inferior connector 330C having indicia 331. Indicia 331 includes symbol 331C indicating that the connector is the left inferior connector. FIG. 28 shows right inferior connector 330D having indicia 331. Indicia 331 includes symbol 33 ID indicating that the connector is the right inferior connector. Right connectors are located on the surgeon's right side and left connectors are located on the surgeon's left side.

FIGS. 25-28 show connectors including symbolic indicia to identify each connector. It should be readily apparent to one skilled in the art that other symbols, markings, or words could be used to identify the connectors, and that these modifications are within the scope of the invention as claimed.

Figure 29:
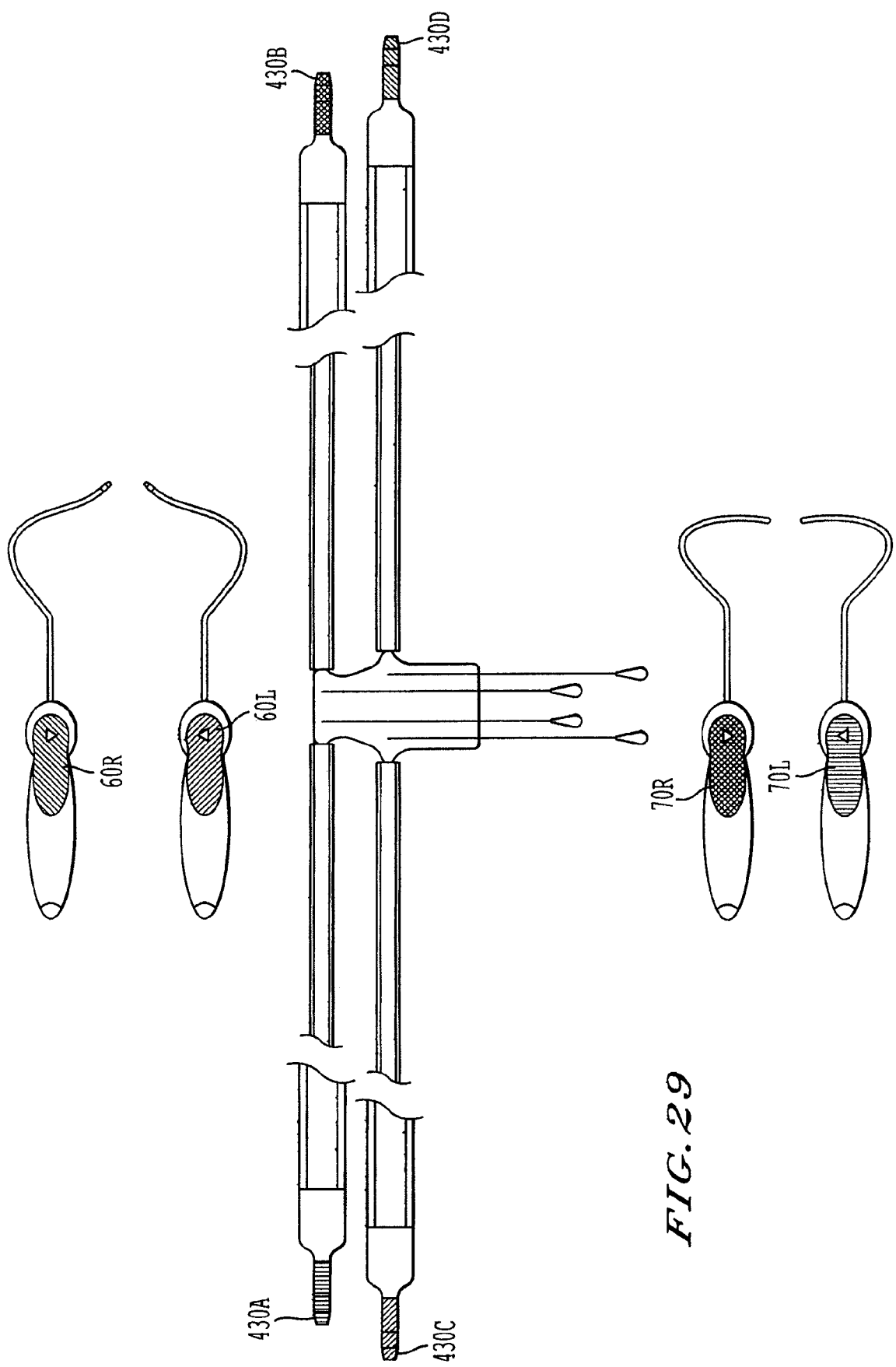
FIG. 29 is a front view of an embodiment of a set of four needles and a support apparatus with four connectors, wherein the connectors are matched to the needles using colors.

FIG. 29 shows another embodiment of the present invention wherein connectors and the handles of the corresponding needles are matching colors. For example, the color of the handle of needle 70L matches the color of connector 430A. The color of the handle of needle 70R matches the color of connector 430B. The color of the handle of needle 60R matches the color of connector 430D. The color of the handle of needle 60L matches the color of connector 430C.

Figure 30:
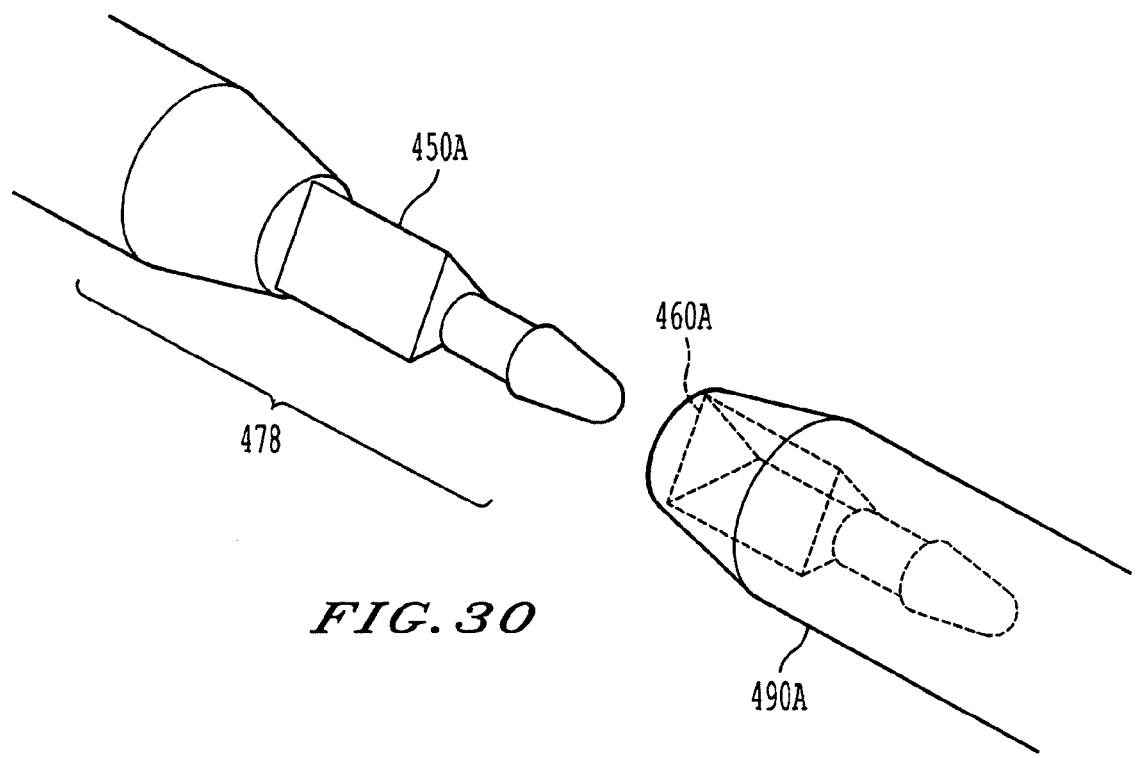
FIG. 30 is a perspective view of a first needle tip and connector of an embodiment of the present invention.
Figure 31:
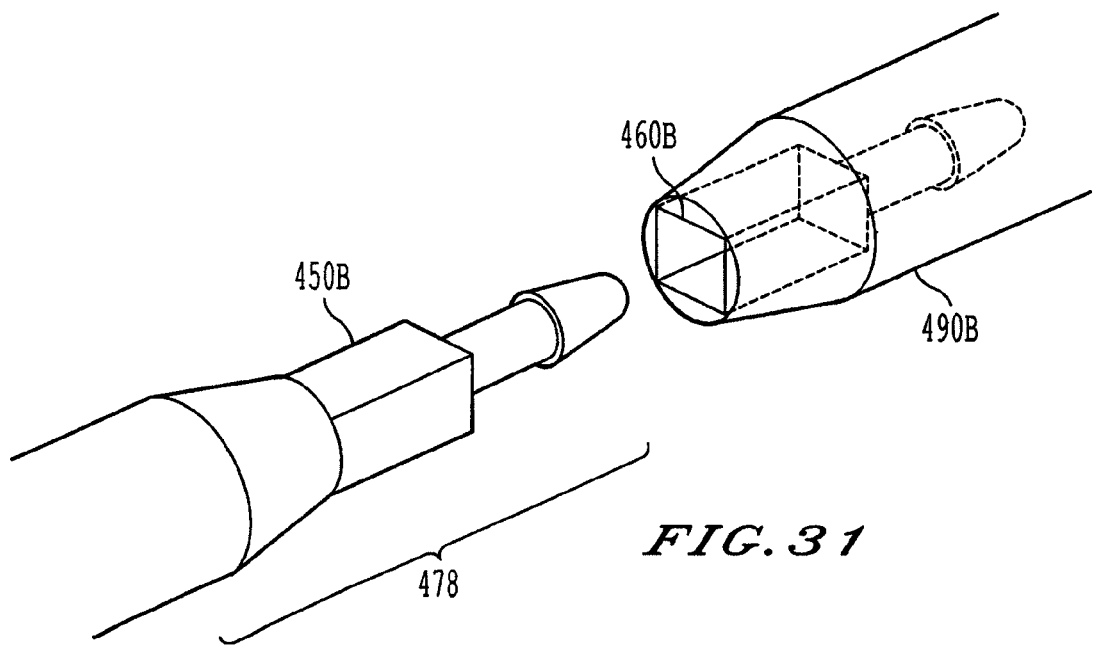
FIG. 31 is a perspective view of a second needle tip and connector of an embodiment of the present invention.
Figure 32:
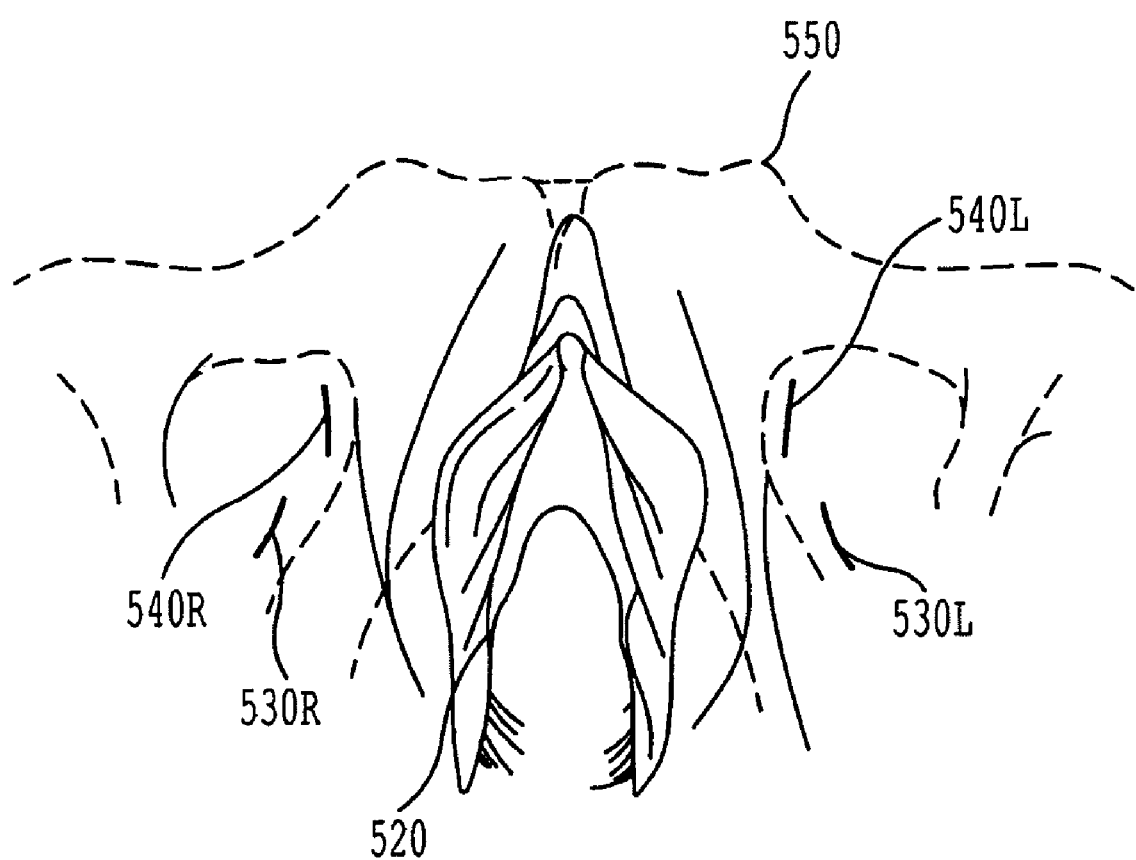
FIG. 32 is a front view of a patient showing the four needle entry incisions.
Figure 33:
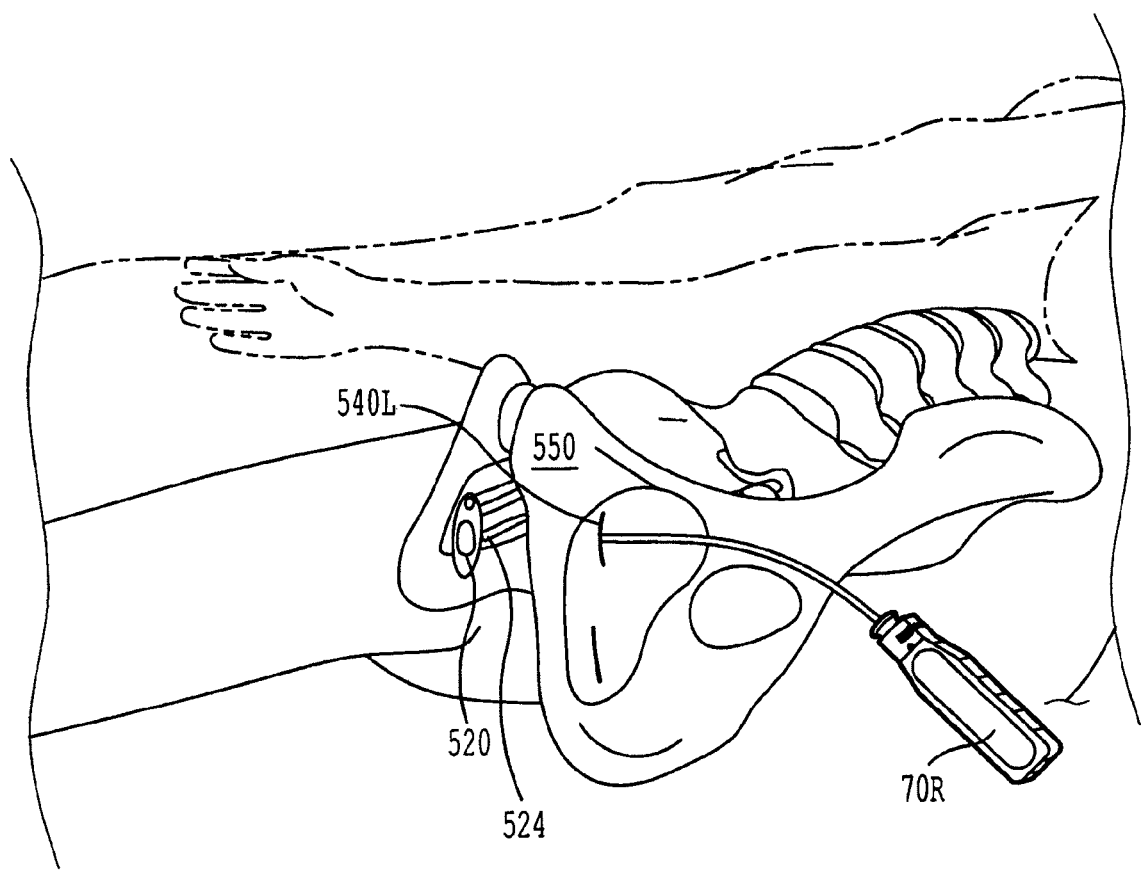
FIG. 33 is a perspective view of a right superior needle tip entering the left superior incision (the superior incision on the patient's left side)
Figure 34:
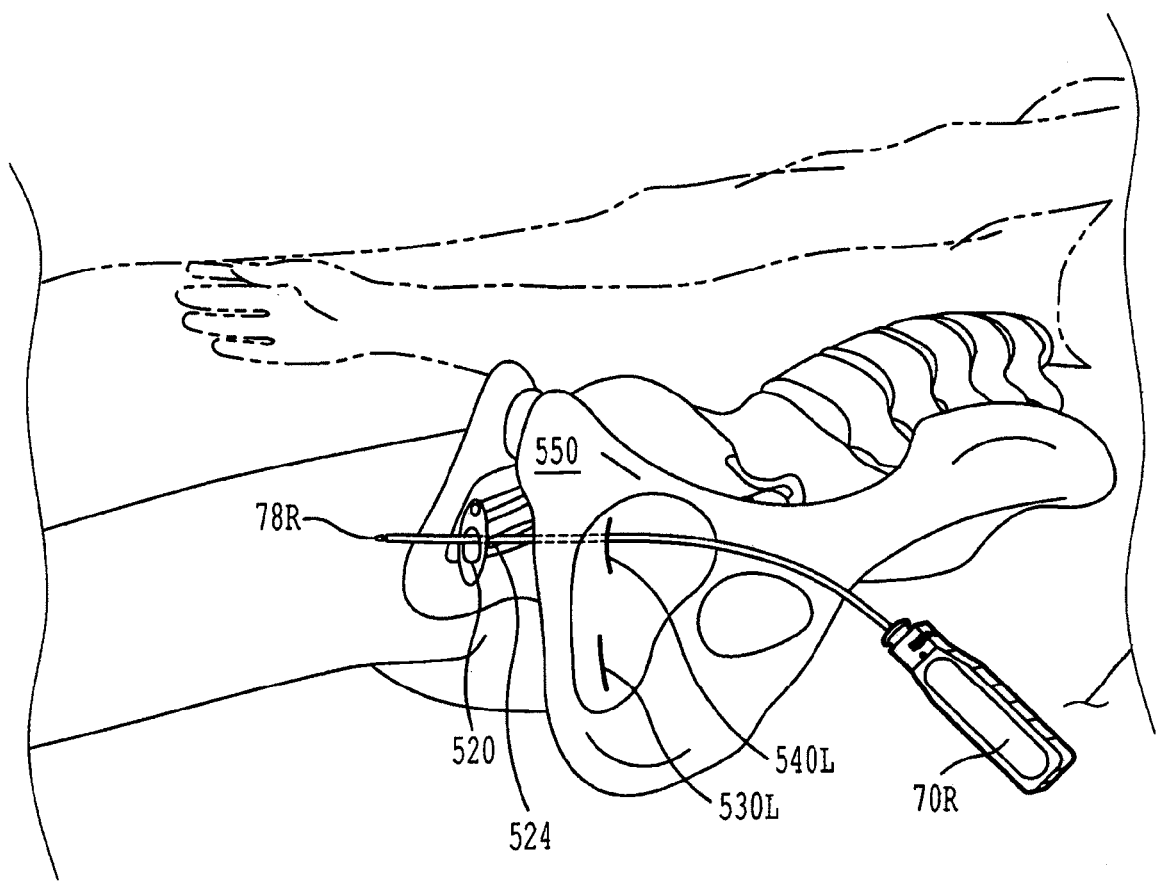
FIG. 34 is a perspective view of a right superior needle tip exiting the vaginal incision.
Figure 35:
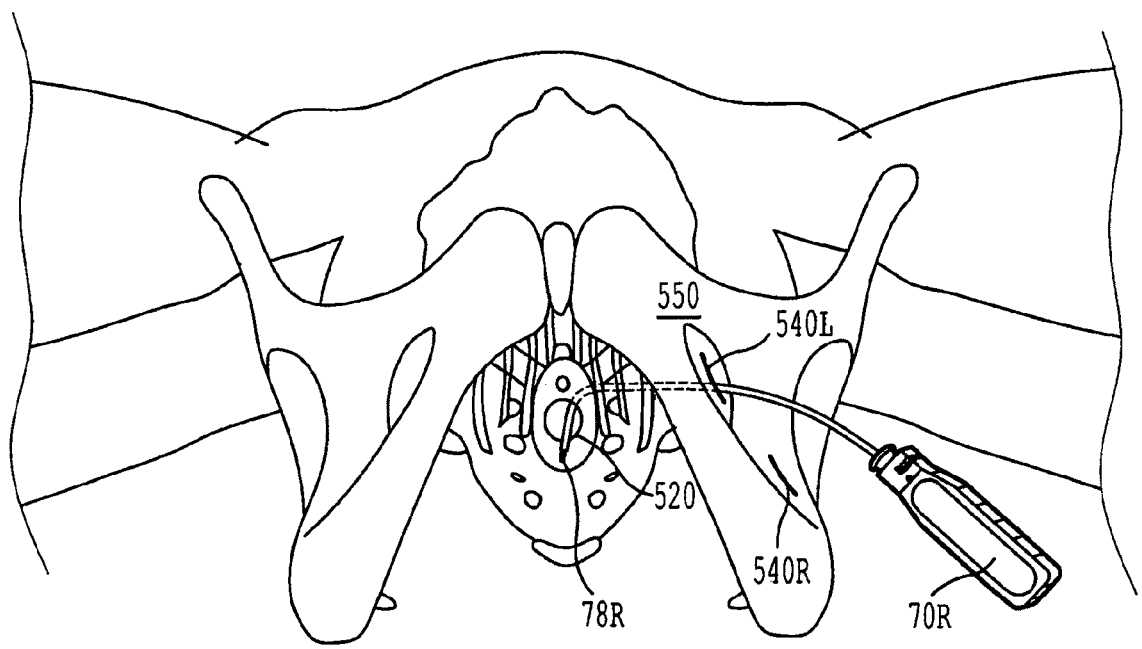
FIG. 35 is a front view of a right superior needle tip exiting the vaginal incision.

FIGS. 30 and 31 are perspective views of a needle tips having a cross sections that are configured to match the cross sections of a connector aperture. FIG. 30 shows that the cross section of portion 450A of needle tip portion 478A is a triangle. The cross section of portion 450A matches triangle shaped aperture 460A in connector 490A. FIG. 31 shows that the cross section of portion 450B of needle tip portion 478B is a square. The cross section of portion 450B matches square shaped aperture 460B in connector 490B.

In one embodiment, each needle tip has a cross section that matches the cross section of an aperture of the corresponding connector, and the tip cross section is incompatible with the other connector apertures. For example, the cross section of the portion 450A, a triangle, would not fit in aperture 460B, a square, and vice versa. Thus, even if the connectors are confused, it is physically impossible for a surgeon to insert the needle tip in the incorrect connector without damaging the tip or connector. It should be readily apparent to one skilled in the art that other shaped tips and apertures are possible, and these modifications are within the scope of the invention as claimed.

Example of a Surgical Procedure

The following description, illustrated in FIGS. 32-39, is an exemplary method for using the disclosed surgical support apparatus 10 having a mesh support member 40. It should be readily apparent to those skilled in the art that modifications may be made to the following method, and these modifications are within the scope of the invention as claimed.

If the embodiment of the surgical support apparatus 110 including a biological support member 140 is used, the biological support member 140 must be prepared before making the vaginal incision. Instructions for preparing the biological support member are given after the present description.

In preparation for surgery, the patient is placed in a modified dorsal lithotomic position with hips flexed, legs elevated in stirrups and buttocks even with edge of the surgical table. The patient's bladder is emptied. A catheter is not required during the procedure, but may aid in identifying the urethra during the procedure. A weighted vaginal retractor or other suitable vaginal retraction is used, if desired.

The length of the vaginal incision is marked with a skin pencil starting below the bladder neck, over the most prominent part of the prolapse, to the lowermost part of the prolapse. (Variations may occur in specific incisions due to individual technique and patient anatomy.) An incision is made over this marking. The incision site may be infiltrated with saline, if desired. An Allis forceps is placed on the incision margin to expose the incision. The patient's bladder is dissected off the vagina up to the lateral sulcus and posterior to the vaginal vault. This dissection allows palpation of the medial edge of the inferior pubic ramus, assisting in guiding the superior and inferior needles to the exit points free from the bladder. The patient's cystocele is then reduced using midline plication, if desired.

Next, markings are made to identify the locations for needle entry incisions. The vaginal dissection is completed prior to marking needle entry incisions to allow for digital palpation along the ischiopubic ramus. The needle entry points are palpated internally and externally with the thumb and index finger before marking, as discussed hereafter.

The edge of the ischiopubic ramus beginning at the level of the vaginal incision is palpated, continuing along the edge of the bone cephalad toward the level of the clitoris denoting where the adductor longus tendon inserts into the pubic ramus. The superior skin incisions are marked approximately at this location and lateral to the edge of the bone. The markings are made according to the same method on both sides (right and left) of the patient's body. Both marks lie in a straight line at the approximate level of the clitoris. The edge of the inferior pubic ramus is palpated until it ends at the bottom of the obturator foramen. The inferior skin incisions are then marked. The inferior skin incisions are located at a point approximately 3 centimeters below and 2 centimeters lateral to the superior marks. Again, the markings are made according to the same method on both sides of the patient's body.

A small vertical stab incision is made over all four markings to provide needle entry incisions. Right superior incision 540R, left superior incision 540L, right inferior incision 530R, and left inferior incision 530L are all shown in FIG. 32. (Right and left with regard to the incisions are the patient's right and left sides.)

The above-described surgical kit is opened. The package integrity is checked to ensure that the kit was not compromised in shipping, and the components of the kit are inspected for damage.

The following method describes the straps on the surgeon's right side (the patient's left side) being surgically installed before the straps on the surgeon's left side (the patient's right side). However, it should be readily apparent to one skilled in the art that the straps of either side could be installed first, and this modification is within the scope of the invention as claimed.

Tip 78R of right superior needle 70R is now inserted through left superior incision 540L, through the left obturator foramen, and then through the vaginal incision 524. Tip of right superior needle 70R is pointed perpendicular to the skin with tip 78R in the left superior incision 540L, shown in FIG. 33. The thumb from the surgeon's right hand is on the outside curve of needle to control the needle movement as it perforates the obturator membrane and muscle. The right thumb pushes the needle through the obturator muscle and membrane. The needle shaft and handle is positioned at a 45° angle to the patient's vertical axis and close to the patient's body. The needle handle is rotated to move the needle tip and curve around the posterior surface of the ischial pubic ramus toward the vaginal incision and index finger. (If the needle tip hits the pubic bone during rotation, the needle is retracted. The needle tip is then penetrated beyond initial insertion depth and rotate again toward the vaginal incision.) The needle tip is palpated with the surgeon's finger. The finger meets the needle tip as it moves around the pubic ramus. (If the needle tip can not be located, the needle tip is retracted to just behind the pubic ramus and advanced again.) The needle tip is guided by the surgeon with the surgeon's finger towards the vaginal incision until the needle tip extends through the vaginal incision, shown in FIGS. 34 and 35.

Figure 36:
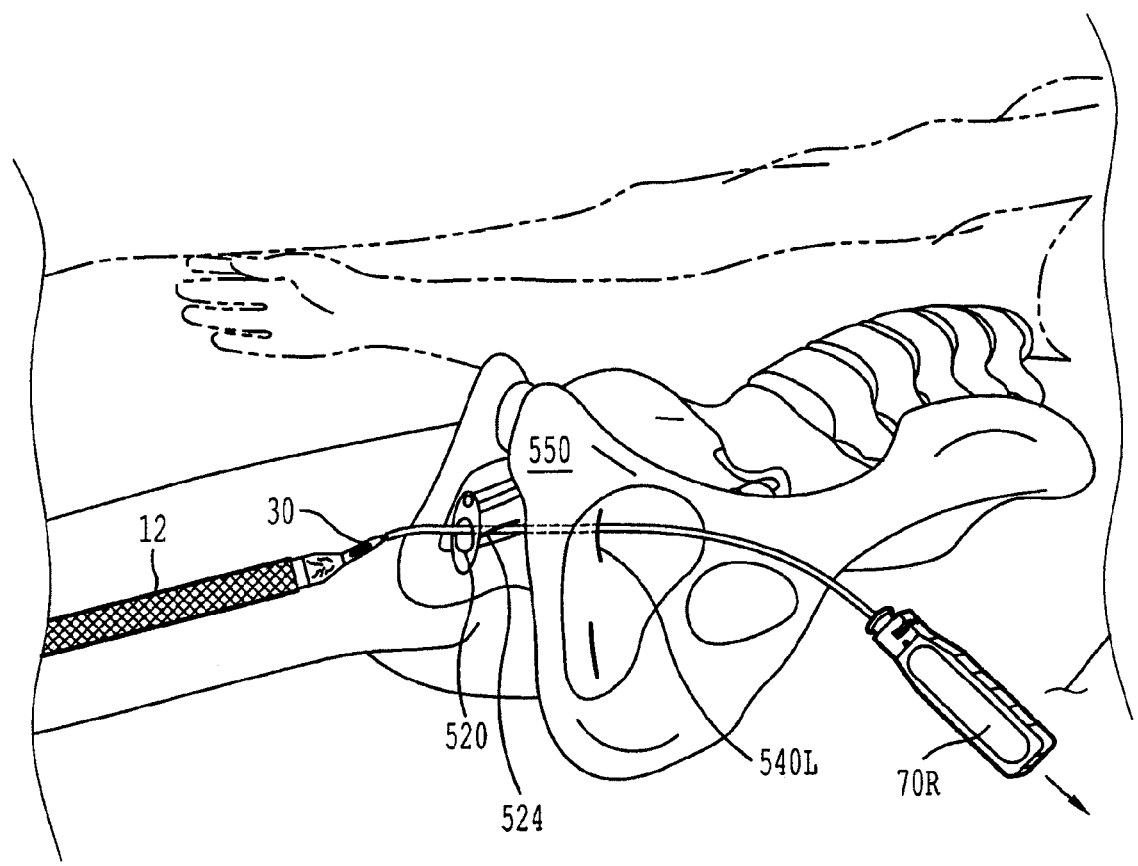
FIG. 36 is a perspective view of a right superior needle tip connected to the right superior connector (the superior connector on the surgeon's right side)

The support member is then oriented so that the tail of the graft is pointing away from the surgeon. (The marking indicia disclosed herein may be used to determine the correct orientation of the support member.) The right superior connector is connected to the tip of the right superior needle, the tip extending out of the vaginal incision, as shown in FIG. 36. The superior needle connectors are closest to the leading edge of the graft that will be below the bladder neck.

Before attaching the connectors, the surgeon ensures that the self-fixating mesh and graft are not twisted, as the connectors are not removable once snapped onto the needle. Once the connector is attached to the needle, the needle is rotated back through the skin incision pulling the connector and associated plastic insertion sheath and graft into position.

Figure 37:
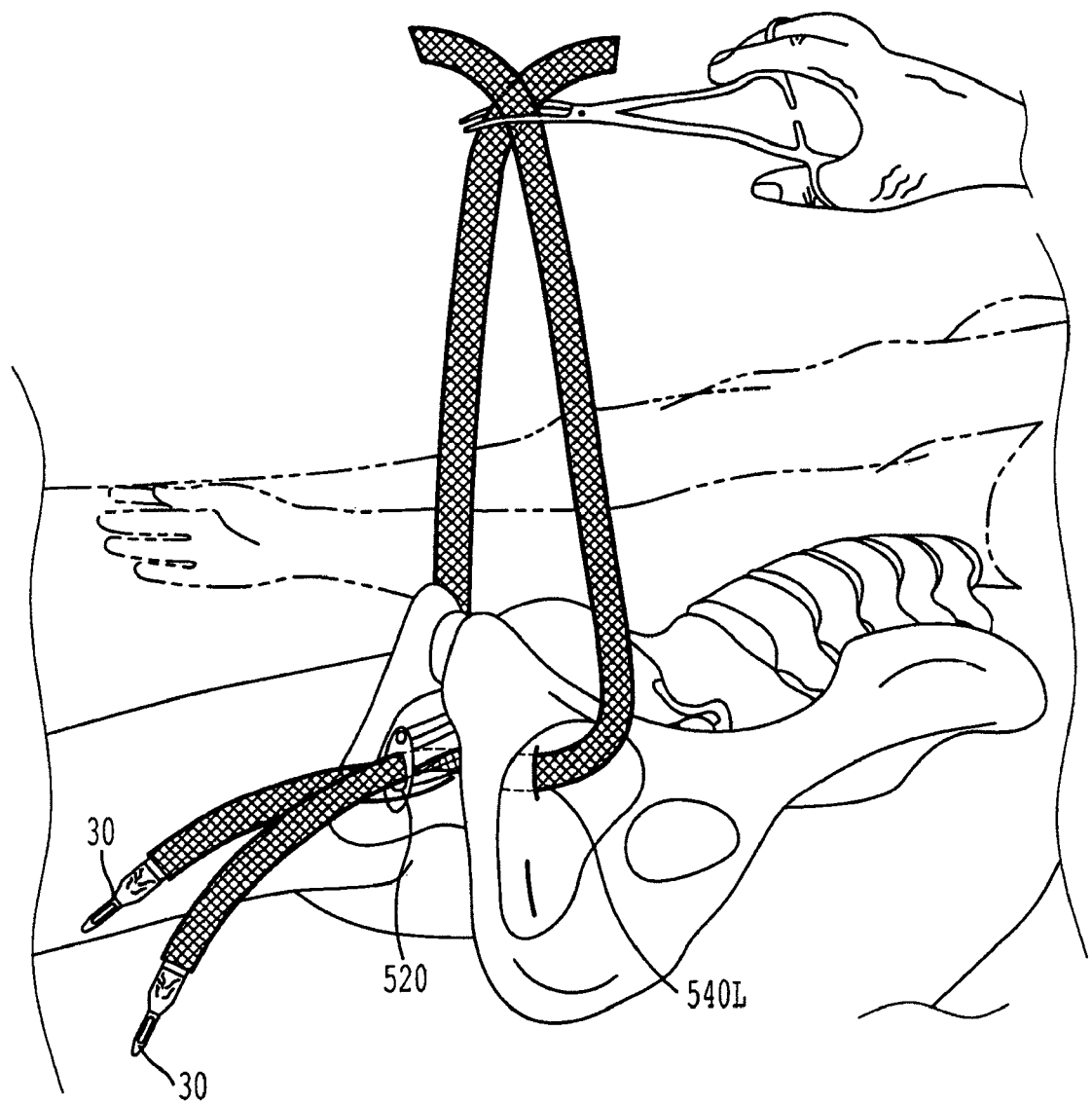
FIG. 37 is a perspective view of the superior straps and the support member in place and the inferior straps extending outside the vaginal incision.

The above process is repeated with the left needle on the patient's right side. The partially implanted apparatus is shown in FIG. 37, with superior straps and support member 40 implanted and the inferior straps extending outside the body through the vaginal incision.

The insertion sheaths and mesh are then cut below the blue mark on the end portion of the plastic sheath and discarded. This step allows the sheath to slide freely relative to the mesh. The sheaths are not removed at this time.

The tip of the right inferior needle is now inserted through left inferior incision 530L, through the left obturator foramen, and then through the vaginal incision. The tip of the right inferior needle is pointed perpendicular to the skin with the tip in the left inferior incision. The exit point for the needle is confirmed to be clear of the bladder wall by the surgeon placing their right index finger at the distal end of the vaginal incision and visualizing where needle exits the distal end of vaginal incision. The surgeon's right thumb is on the outside curve of needle to control the needle movement as it perforates the obturator membrane and muscle. The right thumb pushes the needle through the obturator muscle and membrane.

The needle shaft and handle is positioned parallel to the patient's vertical axis and close to the patient's body. The needle handle is rotated, moving the needle tip and curve toward the distal end of the vaginal incision. The surgeon is careful to avoid buttonholing the fornix to prevent bleeding. The needle tip is palpated as it moves through the distal end of the vaginal incision. The right inferior needle tip is shown extending outside the vaginal incision in FIG. 38.

The right inferior connector is connected to the right inferior needle tip. Again, before attaching the connectors, the surgeon ensures that the self-fixating mesh and graft are not twisted, as the connectors are not removable once snapped onto the needle. The needle is rotated back through the skin incision pulling the connector and associated plastic insertion sheath and graft into position.

The above process is repeated with the left inferior needle on the patient's right side.

The insertion sheath and mesh are then cut below the blue mark on the end portion of the plastic sheath and discarded. This step allows the sheath to slide freely relative to the mesh. The sheaths are not removed at this time.

A cystoscopy is done to check the integrity of the ureters and bladder.

Any vaginal retraction is now removed to allow adjusting the tension of the mesh to reduce bladder bulge. The surgeon confirms the mesh is lying flat and not overlapping under the vaginal wall. The superior leading edge of the support member should be positioned below the bladder neck without tension. The inferior tail portion of the support member should be positioned at the distal end of the vaginal incision or towards the vaginal apex without tension.

If the mesh needs to be loosened, an instrument is placed between the mesh and vaginal wall and pulled down, or away from the vaginal wall until proper tension is achieved.

Each of the four plastic sheaths are removed and discarded, while ensuring the support member graft is not being over tensioned. Once the plastic sheaths are removed, further adjustment is minimized.

If the mesh needs to be tightened, the tensioning suture exiting the skin incision on each side is grasped using a hemostat. The suture is wrapped around the hemostat to improve the grip and pulled up or out to tighten until proper tension is achieved.

To loosen a biologic graft, the surgeon uses a hemostat or a clamp to pull from each of the hanging loosening sutures. The surgeon uses the clamps to pull down and loosen the strap mesh as desired. The surgeon is careful not to pull on tab 18 on loosening suture 16 to loosen the strap mesh.

Figure 39:
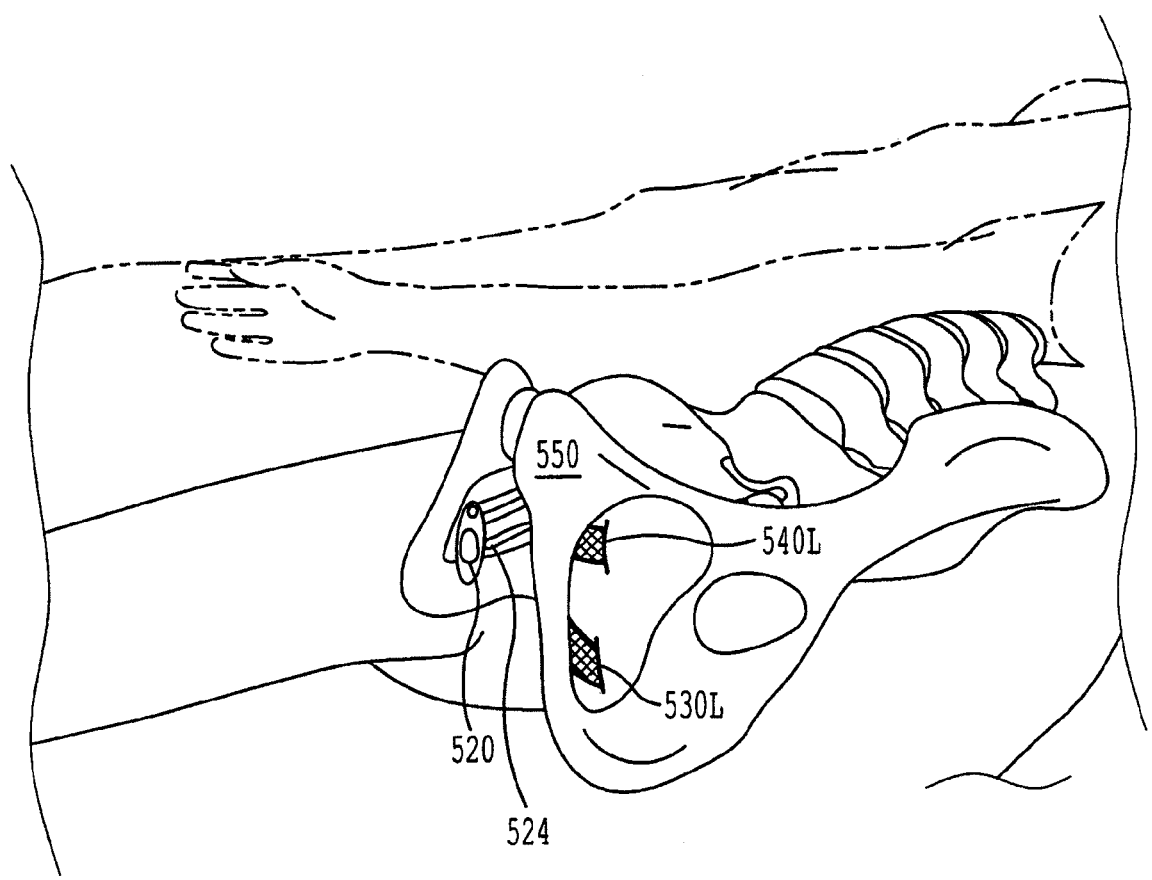
FIG. 39 is a perspective view of all the straps and the support member in place and the sheaths removed.

The surgeon cuts one end of each loosening sutures and pulls tab 18 until the entire loosening suture is removed. The mesh is then trimmed at the level of the subcutaneous tissue and all five incisions are closed. Excess vaginal tissue may be excised. Variations of this step may occur due to individual technique and patient anatomy. The final implanted apparatus is shown in FIG. 39.

After the operation, a catheter and/or vaginal pack can be used at the discretion of the surgeon. It is removed prior to discharge. Antibiotic prophylaxis should be given. The ability of the patient to empty the bladder should be confirmed prior to discharge.

If a biologic graft is used, the following steps are performed before making the vaginal incision. The biologic graft is removed from the package and prepared per included instructions, if needed. A precut biologic is prepared by orienting the graft with the tail portion pointing at the surgeon. Beginning with the right or left inferior landing tabs on the biologic graft (closest to the surgeon), the graft is attached to clamps 150. Attaching the inferior tabs first allows space to attach the two superior mesh appendages with the clamp. The clamps are squeezed to separate mesh tape. The graft material is inserted into the open clamp using printed marks as guides to center the graft. (The printed side of the plastic sheath is facing the surgeon as the surgical apparatus is placed in the body.) The clamp is released to secure graft material. A desired suture is passed up through the clamp using a suturing mark as a guide. The suture is then passed down using the opposite suturing mark as the guide. The passed sutures are then secured using the surgeon's knot(s) of choice. Additional throws are made if needed. The clamp sutures are cut by passing a scissors or a scalpel down the scissors slot on each side of the clamp. The clamps are then removed. The clamp attachment sutures remain with the clamp. The surgeon assesses the attachment of the graft material mesh tape. The protective sheath is slid over the mesh connection to aid deployment.

The preceding steps are repeated on the opposite side of the graft. The sutures are passed such that the attachment knots are all on the same side of the graft. The biologic is placed in a saline bath to keep it hydrated during the remainder of the procedure. The graft tail is trimmed at the time of vaginal marking and dissection to reflect patients anatomy, if needed.

In addition, when using the biologic graft, the surgeon is careful when drawing the strap through the body that the sheath covers the graft connections and that the graft material and graft connections are not damaged.

Figure 40:
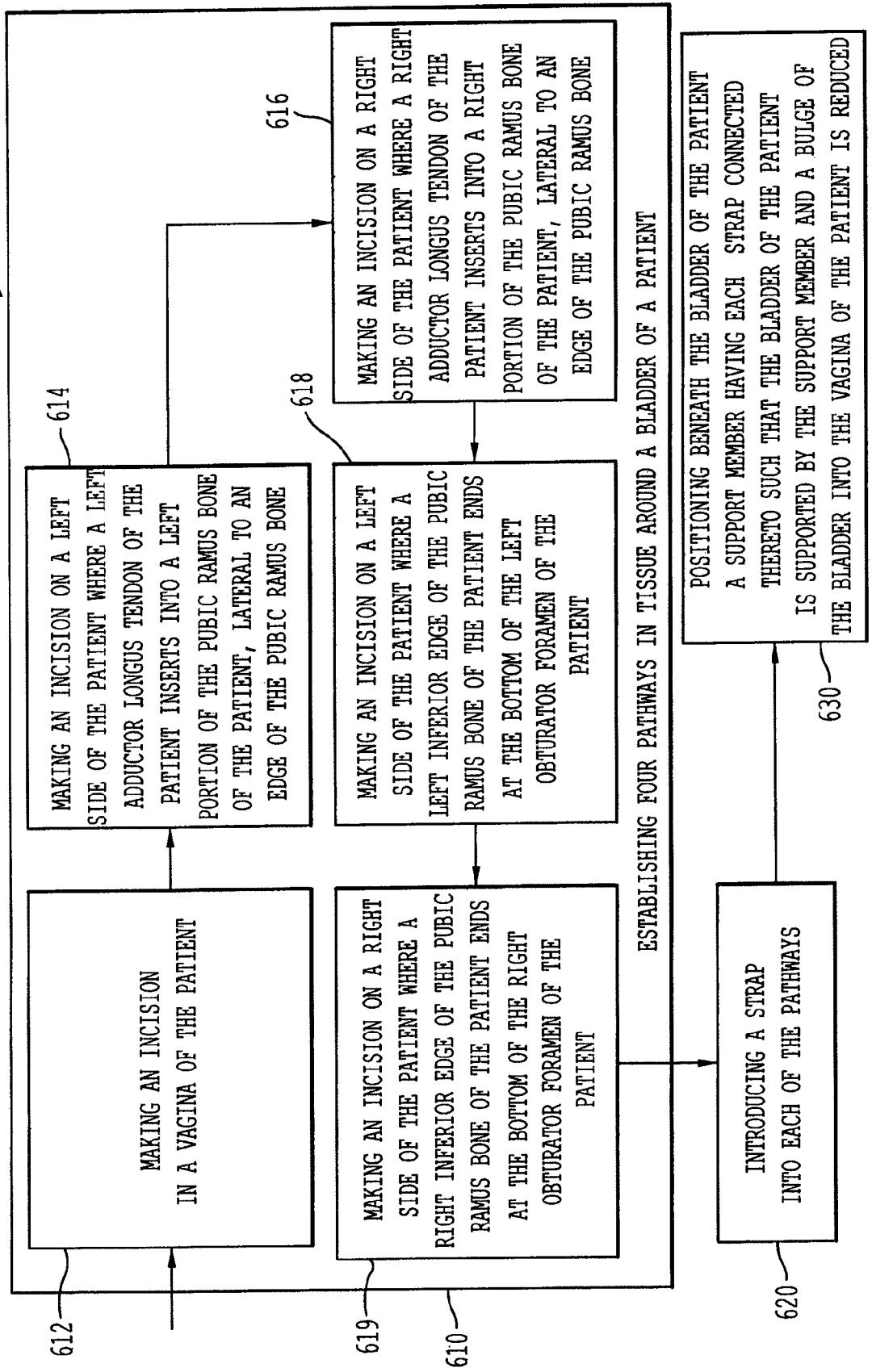
FIG. 40 is a flow chart illustrating a method of practicing the present invention.

FIG. 40 illustrates one embodiment of method of practicing the present invention. Method 600 includes the steps of: establishing four pathways in tissue around a bladder of a patient (step 610), introducing a strap into each of the pathways (step 620), and positioning beneath the bladder of the patient a support member having each strap connected thereto such that the bladder of the patient is supported by the support member and a bulge of the bladder into the vagina of the patient is reduced (step 630). Step 610 comprises the steps of: making an incision in the vagina of the patient (step 612), making an incision on a left side of the patient where a left adductor longus tendon of the patient inserts into a left portion of the pubic ramus bone of the patient, lateral to an edge of the pubic ramus bone (step 614), making an incision on a right side of the patient where a right adductor longus tendon of the patient inserts into a right portion of the pubic ramus bone of the patient, lateral to an edge of the pubic ramus bone (step 616), making an incision on a left side of the patient where a left inferior edge of the pubic ramus bone of the patient ends at the bottom of the left obturator foramen of the patient (step 618), and making an incision on a right side of the patient where a right inferior edge of the pubic ramus bone of the patient ends at the bottom of the right obturator foramen of the patient (step 619).

FIG. 41 illustrates an alternate embodiment of method of practicing the present invention. Method 700 includes the steps of: establishing four pathways in tissue around a bladder of a patient (step 710), atraumatically dilating the pathways (step 720), introducing a strap into each of the pathways while the pathways are atraumatically dilated (step 730), and positioning beneath the bladder of the patient a support member having each strap connected thereto such that the bladder of the patient is supported by the support member and a bulge of the bladder into the vagina of the patient is reduced (step 740). Step 710 comprises the steps of: making an incision in the vagina of the patient (step 712), making an incision on a left side of the patient where a left adductor longus tendon of the patient inserts into a left portion of the pubic ramus bone of the patient, lateral to an edge of the pubic ramus bone (step 714), making an incision on a right side of the patient where a right adductor longus tendon of the patient inserts into a right portion of the pubic ramus bone of the patient, lateral to the edge of the pubic ramus bone (step 716), making an incision on a left side of the patient where a left inferior edge of the pubic ramus bone of the patient ends at the bottom of the left obturator foramen of the patient (step 718), and making an incision on a right side of the patient where a right inferior edge of the pubic ramus bone of the patient ends at the bottom of the right obturator foramen of the patient (step 719).

All patents, patent applications, and publications cited herein are hereby incorporated by reference in their entirety as if individually incorporated.

Obviously, numerous modifications and variations of the present invention are possible in light of the above teachings. It is therefore to be understood that within the scope of the appended claims, the invention may be practiced otherwise than as specifically described herein.

The invention claimed is:

1. A surgical repair kit comprising:
   a support apparatus comprising at least two straps, each of said straps comprising a connector configured to mate with a tip of a needle;
   a first needle configured to extend from an incision on a right side of a patient where a right adductor longus tendon of said patient inserts into a right portion of a pubic ramus bone of said patient, lateral to an edge of said pubic ramus bone, through a right obturator foramen of said patient, to an incision in a vagina of said patient; and
   a second needle configured to extend from an incision on a left side of said patient where a left adductor longus tendon of said patient inserts into a left portion of said pubic ramus bone of said patient, lateral to an edge of said pubic ramus bone, through a left obturator foramen of said patient, to said incision in said vagina of said patient,
   wherein said support apparatus comprises:
      a substantially rectangular member having two short sides and two long sides, a first end of said rectangular member at a first of said two short sides, a second end of said rectangular member at a second of said two short sides;
      a first strap connected to a first long side proximate said first end of said member;
      a second strap connected to a second long side proximate said first end of said member;
      a third strap connected to said first long side proximate a middle portion of said first long side and spaced from said second end; and
      a fourth strap connected to said second long side proximate a middle portion of said second long side and spaced from said second end.

2. The kit recited in claim 1 wherein said support apparatus comprises a biologic graft.

3. The kit recited in claim 2 wherein said biologic graft is pre-attached to said at least two straps.

4. The kit recited in claim 1 wherein said support apparatus comprises: a pair of straps, each strap having a central portion and a connector at each end of said strap; and a biologic graft connected to said central portion of each strap.

5. The kit recited in claim 1 wherein said support apparatus comprises a biologic graft fixed over a knitted support member.

6. The kit recited in claim 1 wherein said support apparatus comprises: a support member knitted with a first bar setting; and a plurality of straps continuously knitted with said support member, said plurality of straps knitted with a second bar setting.

7. The apparatus recited in claim 6 wherein said first bar setting is:
   Bar 1: 1/0, 2/3, 2/1, 2/3, 1/0, 1/2, 1/0, 1/2;
   Bar 2: 1/0, 2/3, 2/3, 1/0; and
   Bar 3: 2/3, 1/0, 1/2, 1/0, 2/3, 2/1, 2/3, 2/1.

8. The kit recited in claim 1 further comprising:
   a third needle configured to extend from an incision on said right side of said patient where a right inferior edge of said pubic ramus bone of said patient ends at a bottom of said right obturator foramen of said patient, through said right obturator foramen of said patient, to said incision in said vagina of said patient; and
   a fourth needle configured to extend from an incision on said left side of said patient where a left inferior edge of said pubic ramus bone of said patient ends at a bottom of said left obturator foramen of said patient, through said left obturator foramen of said patient, to said incision in said vagina of said patient.

9. A kit according to claim 1 wherein:
   each strap comprises a plastic sheath,
   each needle comprises a helical portion,
   each connecter is configured to mate with a needle tip to produce a substantially permanent attachment between the connector and the needle tip.

10. A kit according to claim 1 wherein each needle comprises a handle and each handle comprises a length, a longitudinal axis along the length, opposing major surfaces along the length, opposing minor sides, and a cross section of each handle along the longitudinal axis exhibits an elongate, non-circular form.

11. A kit according to claim 9 wherein each needle comprises a handle and each handle comprises a length, a longitudinal axis along the length, opposing major surfaces along the length, opposing minor sides, and a cross section of each handle along the longitudinal axis exhibits an elongate, non-circular form.

12. A kit according to claim 1 wherein at least one needle has a proximal end and a handle permanently attached to the proximal end.

13. A kit according to claim 9 wherein at least one needle has a proximal end and a handle permanently attached to the proximal end.

14. A kit according to claim 1 wherein each strap comprises a tensioning suture.

15. A kit according to claim 9 wherein each strap comprises a tensioning suture.

16. A kit according to claim 1 wherein a connector includes an aperture configured to mate with a needle tip, the aperture having a shape that corresponds to a shape of the needle tip, the shape allowing entry of the needle tip into the connector at at least one rotational orientation of the needle tip relative to the connector, while preventing entry of the needle tip into the connector at at least one other rotational orientation of the needle tip relative to the connector.

17. A kit according to claim 16 wherein the shape is selected from a shape having a triangle cross section and a shape having a square cross-section.

18. A kit according to claim 9 wherein a connector includes an aperture configured to mate with a needle tip, the aperture having a shape that corresponds to a shape of the needle tip, the shape allowing entry of the needle tip into the connector at at least one rotational orientation of the needle tip relative to the connector, while preventing entry of the needle tip into the connector at at least one other rotational orientation of the needle tip relative to the connector.

19. A kit according to claim 18 wherein the shape is selected from a shape having a triangle cross section and a shape having a square cross-section.

20. A kit according to claim 9 wherein
   each needle comprises a handle and each handle comprises a length, a longitudinal axis along the length, opposing major surfaces along the length, opposing minor sides, and a cross section of each handle along the longitudinal axis exhibits an elongate, non-circular form;

at least one needle has a proximal end and a handle permanently attached to the proximal end, each strap comprises a tensioning suture; and a connector includes an aperture configured to mate with a needle tip, the aperture having a shape that corresponds to a shape of the needle tip, the shape allowing entry of the needle tip into the connector at at least one rotational orientation of the needle tip relative to the connector, while preventing entry of the needle tip into the connector at at least one other rotational orientation of the needle tip relative to the connector.

21. A surgical implant kit comprising:

a support apparatus comprising at least two straps, each of said straps comprising a connector configured to mate with a tip of a needle, each connector having an aperture configured to receive said tip of said needle, wherein at least one connector includes an aperture configured to receive a tip of a needle, the aperture having a shape that corresponds to a shape of the needle tip, the shape allowing entry of the needle tip into the connector at at least one rotational orientation of the needle tip relative to the connector, while preventing entry of the needle tip into the connector at at least one other rotational orientation of the needle tip relative to the connector.

22. A kit according to claim 1 wherein said first strap extends parallel to said third strap and said second strap extends parallel to said fourth strap.

23. A kit according to claim 1 wherein said third strap and said fourth strap are parallel to the first end.

24. A kit according to claim 1 wherein said rectangular member has a length taken in the direction of the two long sides and a width taken in the direction of the two short sides, and wherein the length is greater than the width.

25. A kit according to claim 24 wherein each of said first strap, second strap, third strap, and fourth strap extends from said rectangular member in directions parallel to a two short side.

26. A kit according to claim 1 wherein the two short sides are parallel to one another, and least a portion of one of the two long sides is parallel to at least a portion of the other of the two long sides.

* * * * *